United States Patent [19]

Briggs et al.

[11] Patent Number: 4,822,925
[45] Date of Patent: Apr. 18, 1989

[54] ORGANOSALTS OF METALATE ANIONS AND PROCESS FOR THE PRODUCTION OF ALKYLENE GLYCOLS THEREWITH

[75] Inventors: John R. Briggs; John H. Robson, both of Charleston, W. Va.

[73] Assignee: Union Carbide Corporation, Danbury, Conn.

[21] Appl. No.: 11,748

[22] Filed: Feb. 6, 1987

Related U.S. Application Data

[62] Division of Ser. No. 594,264, Mar. 28, 1984, Pat. No. 4,607,045.

[51] Int. Cl.$^4$ .................. C07E 31/18; C07E 31/24
[52] U.S. Cl. .................... 568/853; 556/20; 556/21; 556/42; 556/57; 568/716; 568/763; 568/778; 568/795; 568/811; 568/821; 568/822; 568/839; 568/851; 568/852; 568/858; 568/859; 568/867
[58] Field of Search .............. 556/20, 21, 42, 57; 568/716, 763, 778, 795, 811, 821, 822, 838, 839, 851, 852, 853, 858, 859, 867

[56] References Cited

U.S. PATENT DOCUMENTS 3,778,451 12/1973 Poite ..................... 556/20 UX

Primary Examiner—Paul F. Shaver
Attorney, Agent, or Firm—Morris N. Reinisch

[57] ABSTRACT

Novel vicinal dioxyalkylene organometalates comprising a cation having a hydrocarbyl-containing substituent are disclosed. The vicinal dioxyalkylene organometalates can be reacted with water to yield alkylene glycols.

10 Claims, No Drawings

ORGANOSALTS OF METALATE ANIONS AND PROCESS FOR THE PRODUCTION OF ALKYLENE GLYCOLS THEREWITH

This application is a division of prior U.S. application Ser. No. 594,264, filed Mar. 28, 1984, now U.S. Pat. No. 4,667,045.

This invention relates to organometalate-containing compounds and to processes for the production of alkylene glycols from alkylene oxides and water involving the use of such compounds. The compounds of this invention are organosalts of metalate anion having at least one cyclic alkylene dioxy moiety thereon. A metalate anion is characterized as being an anion of a polyvalent metallic element with oxygen bonded thereto. The compounds are useful for the preparation of alkylene glycols by contact with water, either as a liquid or vapor.

INTRODUCTION TO COMPOUNDS HAVING METAL AND ORGANIC-CONTAINING MOIETIES

Various organometalates have been disclosed. For instance, Kroenke, in U.S. Pat. No. 4,217,292, issued Aug. 12, 1980, describes amine molybdates prepared by reacting molybdenum trioxide with an amine in an aqueous medium that is essentially free of acid and contains a water-soluble ammonium and/or metal salt of an acid. More recently Kroenke, in U.S. Pat. Nos. 4,406,837; 4,406,838; 4,406,839; and 4,406,840, all issued on Sept. 27, 183, disclosed organo-containing ammonium and amine molybdates. In U.S. Pat. No. 4,406,837, methyltricaprylammonium molybdates are prepared by reacting ammonium dimolybdate with methyltricaprylammonium chloride in an acidic aqueous medium. In U.S. Pat. No. 4,406,838, trioctylammonium molybdates are prepared by reacting ammonium dimolybdate with trioctyl amine in an acidic aqueous medium. In U.S. Pat. No. 4,406,840, tri(tridecyl)ammonium molybdates are prepared by reacting ammonium dimolybdate with tri(tridecyl)amine in an acidic aqueous medium. A process for preparing amine molybdates is disclosed in U.S. Pat. No. 4,406,839 in which a two liquid phase reaction mixture is employed. A molybdenum reactant (such as molybdenum trioxide, molybdic acid or salt) is provided in solution in an aqueous phase, and an amine or amine salt reactant (such as primary, secondary or tertiary amines or quaternary ammonium salts) is or becomes dissolved in an immiscible organic phase. The amine molybdate is dissolved in the organic phase. An inorganic acid is preferably added to the reaction mixture.

Abramson, et al., in U.S. Pat. No. 4,412,956, issued Nov. 1, 1983, disclose a process for making alkyl vanadates by reacting vanadium pentoxide with an alkyl alcohol in the presence of a basic nitrogenous compound which is described as a catalyst. The basic nitrogenous compounds disclosed include ammonia and ammonium compounds, amines, formamide compounds, urea, pyridine, guanidine carbonate and the like.

A. Martinsen et al., in "Preparation and Properties of Some Bis(triphenylphosphine)iminium Salts, [(Ph₃P)₂N]X", Acta Chemica Scandinavica, A 31 (1977) No. 8, pages 645 to 650, describe the preparation of bis(triphenylphosphine)iminium salts by precipitation from a warm, aqueous reaction medium employing the corresponding chloride salt and an alkali metal salt of the desired anion. Various anions disclosed by the authors include chromate, sulfate, nitrate and nitrite.

The compounds previously disclosed have been attributed to have various utilities. For example, the molybdates disclosed by Kroenke are described as smoke retardant additives for vinyl chloride polymer compositions.

Organomolybdenum compounds have been proposed, for instance, as catalysts for the oxidation of certain ethylenically unsaturated compounds, e.g., for the epoxidation of certain olefinic compounds. For example, in U.S. Pat. No. 3,668,227, issued June 6, 1972, a molybdenum alkylene-dioxy-derivative is prepared by reacting an organomolybdenum compound, e.g., molybdenum acetylacetonate, with an organic material having vicinal hydroxyl groups. The organo-molybdenum compounds are represented by the patentees as having the general formulae:

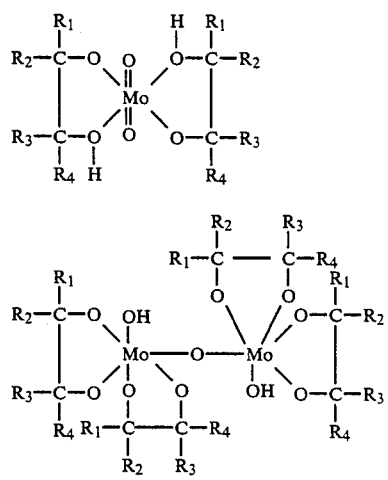

wherein each of $R_1$, $R_2$, $R_3$ and $R_4$ is hydrogen, hydrocarbyl of 1 to 10 carbons, —C(O)R, —NO₂ or $R_1$ and $R_4$ or $R_2$ and $R_3$ may form a bivalent hydrocarbon radical. See also U.S. Pat. No. 3,991,090, issued Nov. 9, 1976.

Organic soluble molybdenum-containing catalysts are disclosed in U.S. Pat. No. 3,480,563, and are prepared by reacting molybdenum trioxide with a monohydric primary saturated alcohol such as octanol-1 or with a polyalkylene glycol monoalkyl ether such as diethylene glycol monomethyl ether. These catalysts are also disclosed as being useful for the epoxidation of olefins.

R. A. Sheldon in "Molybdenum-Catalyzed Epoxidation of Olefins with Alkyl Hydroperoxides", Recl. Trav. Chim. Pays-Bas, 92, p. 253, et seq., (1973) proposed mechanisms for the epoxidation of olefins in which a transfer of an oxygen atom from a Mo(VI)-hydroperoxide complex to an olefin would occur via a cyclic transition state analogous to that for the epoxidation of olefins with organic per-acids. He states that the coordination of the hydroperoxide to Mo(VI) renders the peroxidic oxygen atoms more electrophilic, thereby facilitating nucleophilic attack by the olefin molecule. Thus the polymolybdenum complex acts as a Lewis acid. He further states that the nature of the ligands surrounding the molybdenum should affect the Lewis acidity of the catalyst, and hence the rate of reaction.

In a subsequent article, "Molybdenum-Catalyzed Epoxidation of Olefins with Alkyl Hydroperoxides, II.

Isolation and Structure of the Catalyst", *Recl. Trav. Chim. Pays-Bas,* 92, p. 367, et seq. (1973), R. A. Sheldon states that the molybdenum species which forms during the epoxidation reaction is a Mo(VI)-diol complex, regardless of whether molybdenum hexacarbonyl or molybdenum acetylacetonate had been initially employed, that is, the diol complexes are formed in situ via reaction with the epoxide in the presence of the hydroperoxide. The diol complexes are depicted as having the structure:

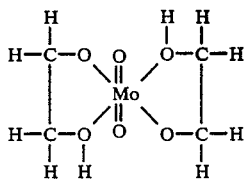

C. L. G. Huch, et al., in Romanian Pat. No. 76,785, issued May 30, 1981 (*Chemical Abstracts* 99:121790k, 1983) disclose dioxomolybdenum bis(1,2-propanediolate) as a catalyst for alkene epoxidation. The preparation disclosed was the reaction of molybdic acid and 1,2-propanediol in an aromatic hydrocarbon reaction medium.

E. Lavayssieve, et al., in "Formation et Caracterisation de Germanones $R_2Ge=O$ a Partir d'Heterocycles Germanies", *Journal of Organometallic Chemistry,* Volume 154, pages C9–C12 (1978), disclose ethyl germadioxolane having the structure

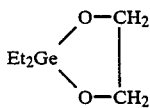

INTRODUCTION TO ALKYLENE GLYCOLS

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology,* Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially-attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

The hydrolysis reaction proceeds uncatalyzed; however, the presence of acids or bases enhances the rate of reaction. Acid and base catalysts, however, do have shortcomings. For instance, base catalysts are generally not selective to the formation of the monoglycol product and acid catalysts are typically associated with corrosion problems. Hence, commercial processes typically utilize relatively neutral hydrolysis conditions (for instance, pH 6–10).

Representative of the numerous acid catalysts that have been suggested for use in the hydration of alkylene oxides include fluorinated alkyl sulfonic acid ion exchange resins (U.S. Pat. No. 4,165,440, issued Aug. 21, 1979); carboxylic acids and halogen acids (U.S. Pat. No. 4,112,054, issued Sept. 5, 1978); strong acid cation exchange resins (U.S. Pat. No. 4,107,221, issued Aug. 15, 1978); aliphatic mono- and/or polycarboxylic acids (U.S. Pat. No. 3,933,923, issued Jan. 20, 1976); cationic exchange resins (U.S. Pat. No. 3,062,889, issued Nov. 6, 1962); acidic zeolites (U.S. Pat. No. 3,028,434, issued Apr. 3, 1962); sulfur dioxide (U.S. Pat. No. 2,807,651, issued Sept. 24, 1957); trihalogen acetic acids (U.S. Pat. No. 2,427,417, issued June 7, 1949); and copper-promoted aluminum phosphate (U.S. Pat. No. 4,014,945, issued Mar. 29, 1977).

In addition to the acid catalysts, numerous catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Pat. No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Various metal-containing compounds, including metal oxides, have been proposed as catalysts for the hydrolysis of alkylene oxides. For example, U.S. Pat. No. 2,141,443, issued Dec. 27, 1938, discloses the production of glycols by the reaction of alkylene oxide with water in the presence of a dehydrating metal oxide, for example, alumina, thoria, or oxides or tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water followed by drying the catalyst. Similarly, U.S. Pat. No. 2,807,651, issued Sept. 24, 1957, states that it is known to catalyze the reaction of an alkylene oxide and water by alkali metal bases, alcoholates, oxides of titanium, tungsten and thorium.

Many metals such as vanadium, molybdenum, tungsten, titanium, chromium, zirconium, selenium, tellurium, tantalum, rhenium, uranium and niobium, have also been proposed as components for catalysts for preparing 1,2-epoxides of alpha-olefins and organic hydroperoxides and often are present during a subsequent hydrolysis reaction. For instance, Examples I and III of U.S. Pat. No. 3,475,499, issued Oct. 28, 1969, disclose that a mixture of normal alpha-olefins containing 11 to 15 carbon atoms was epoxidized with ethylbenzene hydroperoxide in the presence of molybdenum naphthanate catalyst. After distillation, the bottoms, which contained the 1,2-epoxides and the molybdenum-containing catalyst, were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture sould be adjusted to a value in the range of 5 to 10.

Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228, published July 25, 1981, is directed to processes for producing highly pure alkylene glycols. The disclosure is directed to a distillation procedure for recovery of a molybdenum and/or tungsten-containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

U.S. patent application Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, an iron are suggested cations. It is also disclosed that the vanadate may be introduced into the reaction system in the salt form or on a support such as silica, alumina, zeolites and clay. Since the vanadate ion is water-soluble, it can be lost from the reaction system and means must be provided to recover it from the effluent from the reaction zone.

Unfortunately, insoluble salts of metavanadate, such as calcium metavanadate, as well as insoluble molybdate, tungstate, etc., and other metalate salts do not appear to provide the selectivity toward the monoglycol products which is achievable with the water-soluble salts. Hence, problems with the recovery of the water-soluble salts are significant factors in considering the use of the technology on a commercial scale.

OVERVIEW OF THE INVENTION

The compounds of this invention are vicinal dioxyalkylene organometalates comprising a cation having a hydrocarbyl substituent. In an aspect of the invention, the compounds of this invention can be characterized as being an adduct of (a) one molecular unit of an organometalate comprising a cation having at least one hydrocarbyl-containing substituent and (b) at least one molecular unit of a vicinal alkylene oxide.

For purposes of facilitating understanding chemical structures, it has been commonplace in the art to ascribe formula depictions to compounds even though it is well recognized that the actual chemical structure may be different. Using such conventional formula depictions, the vicinal dioxyalkylene organometal compounds of this invention may be represented by the formula:

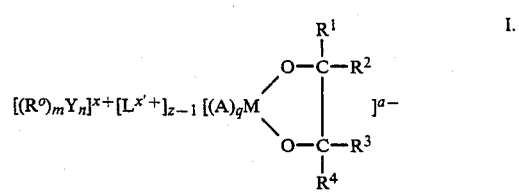

wherein $[(R^0)_m Y_n]^{x+}$ is an organo-containing cation having a positive charge of x, in which organo-containing cation Y is a polyvalent element which is an ionic charge carrying center, each $R^0$ is the same or different and is hydrogen or hydrocarbyl-containing substituent with the proviso that the organo-containing cation has at least one $R^0$ which contains a hydrocarbyl substituent, m is the average number of electron pairs shared by Y with the total $R^0$ groups, n is the number of charge carrying centers, wherein m, n and x are related by the equation $x = n(V-m)$ in which V is the average functional oxidation state of Y wherein each electron pair used by each Y in bonding to $R^0$ is given the value of 1 and the functional oxidation state of Y in the sum of the electron pairs bonding to $R^0$ and x/n, wherein x is an integer of 1 or 2; wherein L is a cation which has a positive charge of x' and which may be the same or different from the organo-containing cation, where x' is usually 1 or 2; wherein z is the number of organo-containing cations which is usually from 1 to 3 or 4; and wherein

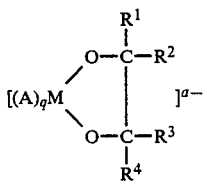

is a vicinal dioxyalkylene organometalate anion having a negative charge of a, in which a equals the amount of $x + [(z-1)(x')]$, M is a polyvalent metal having a functional positive oxidation state of w wherein the absolute value of w equals the absolute value of (q+2), A is a substituent to fill the remaining valencies (q) of M; and $R^1$, $R^2$, $R^3$ and $R^4$ are the same or different and are hydrogen or hydrocarbyl-containing substituents, e.g., of up to about 20 carbon atoms.

The hydrocarbyl-containing substituents useful in the organo-containing cation contain at least one carbon atom, frequently at least four carbon atoms, and may be further substituted with moieties that are not reactive with the anion. L may be ay suitable cation and often is another organo-containing cation or a non-organo-containing cation such as an alkali or alkaline earth metal or an ammonium or phosphonium cation, and serves to balance the charge of the vicinal dioxyalkylene organometalate anion. The substituent A in the vicinal dioxyalkylene organometalate anion may be any suitable substituent and may form another vicinal dioxyalkylene group.

The vicinal dioxyalkylene organometalate compounds of this invention yield alkylene glycols when contacted with water. The alkylene glycol product may be represented by the formula

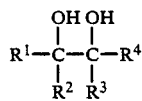  II.

and the resulting metalate (hereinafter referred to as an organometalate) may be represented by the formula

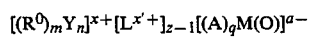  III.

The vicinal dioxyalkylene organometalate of this invention may be prepared by contacting a compound of Formula III with a vicinal alkylene oxide of the formula

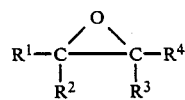

(wherein $R^1$, $R^2$, $R^3$ and $R_4$ are as set forth in Formula I) under temperatures and pressures sufficient to form the vicinal dioxyalkylene organometalate as illustrated in Formula I. Accordingly, the anion

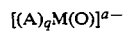

is one which is reactive with alkylene oxides.

Thus, by contacting the vicinal dioxyalkylene organometalate of Formula I with water and then regenerating the vicinal dioxyalkylene organometalate with alkylene oxide, a cyclic process can be provided for the hydrolysis of alkylene oxide to the corresponding alkylene glycol. It has been found that this process proceeds with high selectivity to the monoalkylene glycol product and, depending on the specific technique employed in effecting the reaction, selectivities of substantially one hundred percent of the monoalkylene glycol can be obtained.

Advantageously, processes using the vicinal dioxyalkylene organometalates of this invention can be conducted with lower ratios of water than the ratios of water to alkylene oxide currently being employed for the hydrolysis of alkylene oxides in conventional commercial processes without sacrifice in selectivity to the monoalkylene glycol product. Consequently, energy efficiency can be enhanced. Moreover, as many of the vicinal dioxyalkylene organometalates of this invention are relatively stable, the hydrolysis reaction may be conducted under temperature and pressure conditions that are similar to those employed in conventional commercial operations thereby facilitating the adoption of the processes in existing alkylene glycol plants. However, higher or lower temperatures and pressures may be employed.

The preferred vicinal dioxyalkylene organometalates of this invention have at least one $R^O$ substituent iin the organo-containing cation which renders the vicinal dioxyalkylene organometalate and the organometalate preferentially soluble in an organic medium a compared to an aqueous medium. In aspects of this invention the $R^O$ substituents are such that both the vicinal dioxyalkylene organometalate and the organometalate are essentially insoluble in water. Thus, when using these preferred organo-containing cations, the processes for manufacturing alkylene glycol from alkylene oxide and water become more attractive since recovery of the organometalate residue after contact with water is facilitated. For instance, the organometalate residue may be solid and separated from the reaction products by conventional liquid-solid separation techniques or a liquid which is immiscible or which is extractable into an immiscible organic phase.

DESCRIPTION OF THE VICINAL DIOXYALKYLENE ORGANOMETALATES

The metal in the vicinal dioxyalkylene organometalates of this invention is polyvalent, e.g., having a positive functional oxidation state, e.g., of at least +3, say +4 to +6 or +7, and may be a transition metal. The preferred metals are those which provide a vicinal dioxyalkylene metalate that, when contacted with water, yields a metalate anion that is reactive with alkylene oxide. These metalate anions are characterized by an anionic structure containing at least one metal atom and at least one oxygen ligand conventionally characterized as double-bonded oxygen atom as may be illustrated by the following formula:

$$[(A)_qM(O)]^{a-}$$

wherein a is the negative charge of the anion which is between −1 and −4, A is one or more substituents to fill the remaining valencies (q) of M may be the same or different and may be, for instance, double-bonded oxygen; an organic radical such as an alkyl, alkoxy, acyl, aryl, amino, phosphine, etc., usually of 1 to about 12 carbon atoms; halogen (e.g., chlorine, fluorine, iodine); —O— or —S— wherein the remaining valency of the oxygen atom is in free ionic form or is bonded to the organo-containing cation or L. Most commonly, especially when the vicinal dioxyalkylene organometalate is generated by the reaction of the organometalate with alkylene oxide, A is —O— or =O. Even when the A in the starting organometalate is other than —O—, e.g., chlorine, it is possible that the original substituent becomes replaced by —O— in the course of generating the vicinal dioxyalkylene organometalate. Hence, the vicinal dioxyalkylene organometalate anion often is represented by the structure

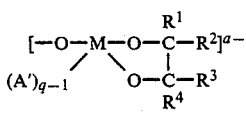

wherein each A' is =O or —O—.

Particularly preferred metals for the metalates include the metals in groups Vb and VIb of the periodic chart such as vanadium, molybdenum and tungsten, although other metals such as rhenium and germanium may also find application. Representative metalates which readily form the dioxyalkylene organometalates when contacted with alkylene oxide and yield alkylene glycol when contacted with water include molybdate, tungstate, metavanadate, hydrogen pyrovanadate and pyrovanadate (although because of the complex chemistry associated with many metalate anions, the precise structure of the operative specie or species may be different). Frequently, the metalate anion comprises at least one anion conventionally characterized by the formulae $[MoO_4]^{2-}$, $[VO_3]^-$, $[V_2O_7H]^{3-}$, $[V_2O_7]^{4-}$, and $[WO_4]^{2-}$;

however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the metalate anion added) appear to exhibit little, if any, activity for enhancing selectivity.

In an aspect of the invention, the metal for the metalate is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as in rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by rhenium as the rhenate anion, then the metal as the metalate is probably less nucleophilic than rhenium as rhenate with respect to ethylene oxide. If the production of diethylene glycol and polyethylene glycol is greater than that provided with orthovanadate, regardless of the rate of formation of ethylene glycols, then the metal as the metalate is probably less electrophilic than orthovanadate with respect to ethylene oxide.

The $R^1$, $R^2$, $R^3$, and $R^4$ substituents of the vicinal dioxyalkylene organometalate may be the same or different and are hydrogen, or hydrocarbyl, including substituted hydrocarbyl, of 1 to 20, preferably 1 to 6 or 8 carbons. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms.

Frequently, the anion comprises an anion conventionally characterized by the formulae $[C_2H_4O_2MoO_3]^{2-}$, $[(C_2H_4O_2)_2MoO_2]^{2-}$, $[C_2H_4O_2VO_2]^{1-}$, or $[C_2H_4O_2WO_3]^{2-}$ or $[(C_2H_4O_2)_2WO_2]^{2-}$ and possibly $[C_2H_4O_2V_2O_6]^{4-}$ or $[C_2H_4O_2V_2O_6H]^{3-}$;

however, it is recognized that the chemistry of these metalates, particularly the vanadates, is complex, and the exact chemical formula may prove to be different. Indeed, especially with respect to vanadates, a mixture of species may be present and the predominance and identity of the species may differ depending on the temperature, solvent, and pH of the metalate-containing solution.

The organo-containing cation of the vicinal dioxyalkylene organometalate is characterized as having a polyvalent element, Y. Polyvalent elements include the elements in Groups Va and VIa of the periodic chart, such as nitrogen, phosphorous, arsenic, antimony, bismuth, sulfur, selenium and tellurium. Advantageously, the cation is stable in the presence of water. Hence, Y is preferably not oxygen. From the standpoints of stability and availability, Y is usually phosphorous, sulfur and especially nitrogen.

When used in the production of alkylene glycols from alkylene oxides by contact with water, it is preferred that if the cation is to be in solution that it has a marked solubility in an organic medium and is preferentially soluble in the organic medium as compared to water. (Because of the reactivity of the vicinal dioxyalkylene organometalate with water, the water solubility parameter is determined with respect to the organometalate product.) Often, the hydrocarbyl-containing component of the cation is sufficient to impart a greater solubility of the organometalate product in a given water-immiscible organic solvent such as toluene than in distilled water at a given temperature, say, 25° C. In some instances, the solubility coefficient is at least about 5 times, say, at least about 20 times, greater in toluene than the solubility coefficient of the organometalate product in distilled water at 25° C. In an aspect of the invention, the organometalate product is substantially insoluble in distilled water, e.g., less than about 50, say, less than about 10, grams of the organometalate will dissolve in a liter of distilled water at 25° C. Some organometalate products are immiscible with distilled water and some are solid at ambient temperatures, for instance, 25° C., or even at temperatures suitable for forming the vicinal dioxyalkylene organometalate from alkylene oxide and organometalate, e.g., about 50° C. to 250° C.

Since the hydrophilicity and organophilicity of the vicinal dioxyalkylene organometalates are influenced by the hydrocarbyl content of the organo-containing cation, it frequently contains at least one substituent having at least four carbon atoms. No theoretical maximum exists for the total number of carbon atoms in any one substituent on Y or in the total substituents on Y.

A substituent may render the vicinal dioxyalkylene organometalate substantionally solid or may be bonded or complexed to an organic or inorganic solid. Copending U.S. patent application Ser. No. (atty docket D-13947), filed on even date herewith, of R. D. Best, J. A. Collier, B. T. Keen and J. H. Robson, herein incorporated by reference, discloses solid supports, e.g., anion exchange resins that have electropositive complexing sites which, among other possibilities, can be quaternary ammonium and quaternary phosphonium moieties that are in association with a metalate anion. These solid supports having metalate anion in association therewith are useful in processes to make alkylene glycol from alkylene oxide. For instance, a styrene-divinyl benzene resin having quaternary ammonium substituents such as DOWEX MSA-1 ™ resin, available from The Dow Chemical Company, can be contacted with an aqueous solution of sodium molybdate to replace the original chloride anion. Such a resin, when employed in the presence of water and alkylene oxide under suitable hydrolysis reaction conditions, e.g., about 100° C. to 120° C., enhances the selectivity to the monoalkylene glycol product.

In one aspect of the invention, Y is a polyvalent element in group Va of the periodic chart, and some of the cation structures may be represented by the formula, e.g., ammoniums, phosphoniums, and arsoniums,

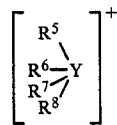

and for members of group VIa of the periodic chart, e.g., sulfoniums, by the formula

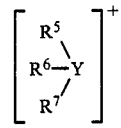

each of $R^5$, $R^6$, $R^7$ and $R^8$ may be the same or different and may combine to form cyclic structures. Exemplary of each of $R^5$, $R^6$, $R^7$ and $R^8$ are hydrogen and hydrocarbyls which may be substituted or unsubstituted and contain at least 1 carbon atom and, preferably, at least one, and most preferably all, contains at least about 4, carbon atoms, e.g., about 4 to 70, and sometimes 4 to 20, carbon atoms. However, at least one of the substituents must be hydrocarbyl-containing.

The hydrocarbyl substituents may be aliphatic or aromatic and include, for example, n-hexyl, cyclohexyl, phenyl, benzyl, naphthyl, and the like. Illustrative of the quaternary ammonium and quaternary phosphonium moieties are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.t., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like.

Another group of organo-containing cations includes the bis(hydrocarbyl-phosphine)iminiums represented by the formula:

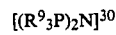

wherein each $R^9$ may be the same or different and may be the same as set forth for $R^5$ to $R^8$. Illustrative of bis(hydrocarbyl-phosphine)iminiums are bis(triphenyl-phosphine)iminium, bis(tribenzyl-phosphine)iminium, bis(trimethyl-phosphine)iminium, bis(tridodecyl-phosphine)iminium, and the like.

A further group of organo-containing cations have the formula:

$$[(R^{11})_r-Y-R^{10}-Y-(R^{11})_r]^{2+}$$

wherein $R^{10}$ is alkylene of 1 to about 6 carbon atoms, $R^{11}$ is hydrogen or hydrocarbyl which may be substituted or unsubstituted and r is 3, such as the quaternized diamines, quaterized diphosphines, etc. Members of this group include
N,N'-bis(trimethyl)propylene diamine,
N,N'-bis(triphenyl)propylene diamine,
N,N'-bis(trioctadecyl)propylene diamine,
P,P'-bis(trimethyl)propylene diphosphine, and the like.

The anion of the vicinal dioxyalkylene organometalate may be associated with cations in addition to the organo-containing cation. These cations, i.e., L of Formula I, may include alkali metals, alkaline earth metals, copper, zinc, iron, ammonium cations, phosphonium cations, sulfonium cations, and other cations includin organic-containing cations, e.g., containing alkyl, alkyoxy, acyl, aryl, amino, phosphino, etc., groups of 1 to about 12 carbons.

The vicinal dioxyalkylene organometalate may be prepared in any convenient manner. A preferred technique is to prepare the organometalate of Formula III and then react it with an alkylene oxide.

The organo-containing metalates may be prepared by any convenient technique. In one general process, a water-soluble salt of the metalate anion is dissolved in water, which is preferably at an elevated temperature, e.g., at least about 35° C. or 40° C., sufficient to maintain the water-soluble salt in solution and is contacted with a salt of the desired organo-containing cation. The anion of the desired cation may be a halide, nitrate, nitrite, sulfate, sulfite, chlorate, chlorite, from organic acids and polyacids such as acetate, propionate, lactate, oxalate, etc., or the like, and the counter ion to the metalate anion may be ammonium or alkali metal (especially sodium, potassium and lithium). The selection of the particular anion and cation to be used as counter ions to the desired cation and metalate anion is usually based on solubility considerations for the reactants and the products, i.e., the salt, formed by the counter ions. In one aspect, the formed organometalate precipitates from the solution. Alternatively, an immiscible organic liquid phase may be employed to extract the organometalate from the aqueous phase for recovery.

Another process for preparing organo-containing metalates involves reacting in an organic medium a heavy metal (e.g., silver) salt of the metalate with a soluble salt of the desired organo-containing cation where the counter ion to the desired cation will react with the silver, e.g., a chloride anion, and form an insoluble salt. The temperatures employed will vary depending upon the nature of the materials; however, often ambient temperature, e.g., 25° C., is suitable and temperatures in the range of −10° to 150° C. may be employed. The organic solvent should be capable of dissolving the metalate-containing reaction product. An illustration of organic solvent is dichloromethane. Such processes are described in more detail in U.S. Pat. No. 4,585,883, of J. R. Briggs, herein incorporated by reference.

It is preferred that the technique employed for making the organo-containing metalate not unduly adversely affect the metalate, e.g., by reduction of the metal of the metalate. As with any preparation technique, some reactants are more readily employed than others.

In order to obtain the organometalate or vicinal dioxyalkylene organometalate, it is not necessry to use the metalate form. Indeed, any form of the metal, M, which will yield the vicinal dioxyalkylene organometalate upon reaction with alkylene oxide and the organometalate and/or upon reaction of the vicinal dioxyalkylene organometalate with water (including in situ during a process of the hydrolysis of alkylene oxide) is believed to be suitable. The metal-containing species may therefore contain halide, e.g., chloride and iodide; sulfide, aliphatic or aromatic hydrocarbon, or similar substituents. The selection of the metalate, or precursor of the metalate, will, in general, be dependent upon the availability of the compound and its processing characteristics and, in the case of the precursors to the metalate, additionally the ability to form the vicinal dioxyalkylene organometalate.

Vicinal alkylene oxides which may be used to produce the vicinal dioxyalkylene organometalate from the organometalate have the general formula:

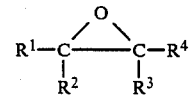

wherein $R^1$, $R^2$, $R^3$ and $R^4$ are as set forth above. Representative of alkylene oxides are ethylene oxide, propylene oxide, butylene oxide, (e.g., isobutylene oxide, 1,2-butylene oxide and 2,3-butylene oxide), pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organohydroperoxide in the presence of a catalyst or by the partial oxidation of an alkene (especially ethylene) with a molecular oxygen-containing gas in the presence of a silver catalyst.

The reaction between the organometalate and the alkylene oxide may be conducted at relatively low temperatures to elevated temperatures, e.g., about −15° C. to 250° C., and should not be at a temperature which is deleterious to the cation or the metalate. With more reactive metalates such as organomolybdates, organotungstates, and organovanadates, the reaction may proceed at lower temperatures, e.g., 0° to 15° C., to form the vicinal dioxyalkylene organometalate. Often the temperature is between about 0° and 200° C., and elevated temperatures are preferred from a standpoint of convenience and compatability with further processing operations. The reaction may be conducted in an anhydrous organic medium which is non-reactive with the alkylene oxide or organometalate, e.g., dichloromethane, 1,1,2-trichloroethane, toluene, benzene, and xylene, or may be conducted in a water-containing medium, especially if isolation of the vicinal dioxyalkylene organometalate is not sought. The hydrolysis reaction generally proceeds more rapidly than the vicinal dioxyalkylene organometalate-forming reaction. However, the reactivity with water enhances the attractiveness of using the vicinal dioxyalkylene organometalates of this invention to prepare alkylene glycols from alkylene oxides. Advantageously, the vicinal dioxyalkylene organometalates are used in processes to prepare alkylene glycol from alkylene oxide and water.

Discussion of Alkylene Glycol Formation

In the processes to form alkylene glycols of Formula II, the organometalate is contacted with alkylene oxide under reaction conditions effective for forming the vicinal dioxyalkylene organometalate. At these conditions it is generally the case that when the vicinal dioxyalkylene organometalate is contacted with water, in liquid or vapor form, the alkylene glycol is readily liberated and the organometalate is generated. Frequently, the alkylene oxide has been purified to avoid the presence of components which may produce troublesome impurities in the alkylene glycol product.

Water is also employed as a reagent for the formation of the corresponding alkylene glycol. Usually the water is of sufficient purity to provide a suitable quality alkylene glycol product. The water may be distilled or demineralized, for example, by ion exchange treatment.

The organometalates may be solid or liquid under reaction conditions. Most often for the sake of convenience, the oraganometalate is dissolved in a solvent which is liquid under the conditions of the reaction. The liquid solvent should be inert to the organometalate and the alkylene oxide, alkylene glycol and water. The selection of suitable solvents is, in part, based on the ability to dissolve and/or miscibility with the organometalate, and preferably, the alkylene oxide has some degree of solubility in the liquid solvent. Frequently, at least about 5, say, at least about 20, grams of organometalate are soluble per liter in the liquid solvent at 25° C. at atmospheric pressure, and some organometalates will be miscible with the solvent in all proportions under reaction conditions.

Exemplary of liquid solvents are alkyl, cycloalkyl and aromatic-containing solvents, especially halogenated alkyl, cycloalkyls and aromatics, such as cyclopentane, cyclohexane, methylcyclohexane, cycloheptane, benzene, toluene, xylene, naphthene, carbon disulfide, dichloromethane, 1,1,2-trichloroethane, carbon tetrachloride, and the like. Silicone oils and mineral oils may also find application. Also, interactive solvents such as 1,2-dimethoxyethane, etc., may be used. Not all the above solvents will be suitable for all of the organometalates of this invention.

It is believed that the reaction to alkylene glycol can proceed by at least two routes. The first route is the conventional route in which alkylene oxide is directly reacted with water. Alternatively, alkylene oxide can react with the organometalate to form the vicinal dioxyalkylene organometalate, which, when contacted with water, liberates alkylene glycol. The specific rate of reaction between the alkylene oxide and metalate will depend, in part, on the alkylene oxide employed and the organometalate employed. When using the vicinal dioxyalkylene organometalates of this invention, the selectivity to the monoglycol product can be enhanced as compared to conventional commercial hydrolysis techniques. Alkylene glycols can be produced from alkylene oxides and water in various manners.

One method which is particularly attractive for providing extremely high selectivities to monoalkylene glycol involves sequentially contacting the organometalate with alkylene oxide to form the vicinal dioxyalkylene organometalate and then contacting the vicinal dioxyalkylene organometalate with water to form the corresponding alkylene glycol. Such processes, which include, inter alia, organometalates are disclosed in copending U.S. Pat. No. 4,564,715, of J. R. Briggs, G. L. O'Connor and J. H. Robson, herein incorporated by reference. Preferably, the reaction between the alkylene oxide and organometalate is conducted in the presence of little, if any, water to minimize or avoid the formation of alkylene glycols which could react with ethylene oxide to form di- and polyglycols. For example, the mole ratio of water to alkylene oxide initially present may often be less than about 0.5:1, say, less than about 0.1:1, and the reaction medium may be substantially free from water. However, in some instances some water may be provided beneficially to enhance the stability of the metalate anion.

Usually, sufficient organometalate is provided for complete reaction with the alkylene oxide, and an excess of organometalate of the amount required for reaction with alkylene oxide on a stoichiometric basis is employed to ensure a substantially complete conversion. However, lesser amounts of organometalate may be employed if desired. Thus, the mole ratio of alkylene oxide to metalate anion is frequently in the range of about 20:1 to 1:20, say, about 5:1 to 0.5:1, and most preferably about 3:1 to 0.9:1. With metalate anions having more than one reactive site for association with alkylene oxide such as some molybdates and tungstates, the amount of metalate anions may be decreased accordingly.

Any unreacted alkylene oxide may be recovered from the vicinal dioxyalkylene organometalate prior to contact with the water or may be passed with the reaction product to contact the water. For the highest selectivity to monoalkylene glycol, it is preferred that the reation alkylene oxide with the organometalate is substantially complete or that the unreacted alkylene oxide is removed prior to contacting water.

The vicinal dioxyalkylene organometalate is then contacted with water or steam to form the corresponding alkylene glycol. The water or steam is frequently provided in excess of the amount required to react with the vicinal dioxyalkylene organometalate and the unreacted alkylene oxide; however, lesser amounts can be employed. Thus, the mole ratio of water or steam to total vicinal dioxyalkylene organometalate and unreacted alkylene oxide may be about 0.5:1 to 50:1. The vicinal dioxyalkylene organometalate-containing phase may be continuously passed through an aqueous phase, or alternatively, steam or water may be passed through it. Hence, the mole ratio of water or steam to the vicinal dioxyalkylene organometalate and unreacted alkylene oxide at a given volume in the reaction menstruum may be greater or lesser than the foregoing mole ratios which are based on total amount of reactants provided to the reaction zone. When employing steam as the source of water for the liberation of alkylene glycol, little, if any, liquid water will be present to be removed from the alkylene glycol product, e.g., by evaporation. Thus, higher ratios of steam to the vicinal dioxyalkylene organometalate and unreacted alkylene oxide may be advantageous, for instance, about 5:1 to 40:1. On the other hand, when water is employed, it must be removed from the alkylene glycol product, and therefore from the standpoint of energy efficiency, lower ratios of water to vicinal dioxyalkylene organometalate reaction product and unreacted alkylene oxide are desirable, for instance, about 1:1 to 5:1.

After the reaction with water, the alkylene glycol can then be separated, e.g., by phase separation, from the organometalate-containing phase which may be suitable for reuse in reacting with alkylene oxide. Hence, this mode of operation is particularly convenient for continuous processes in which the organometalate is recycled.

The sequential process may be conducted in any convenient manner. For example, the process may be conducted in two vessels, the first for conducting the reaction between the organometalate and alkylene oxide and the second for the contact with water or steam to yield the alkylene glycol. It is also possible to conduct the process in a single vessel having several zones; in the first portion of the vessel the organometalate and alkylene oxide are contacted and in a later portion water or steam is introduced. The vessels may be provided with means to promote the contact between the reactants. For example, agitators, packing, trays and other devices for promoting liquid-liquid or gas-liquid contact, as the case may be, may be employed. Either phase may be the continuous phase. By way of illustration, steam may be dispersed as fine bubbles throughout a liquid, metalate-containing phase or a liquid, metalate-containing phase may be dispersed in an aqueous phase.

Another illustrative method for producing alkylene glycol involves maintaining a two liquid phase reaction zone wherein the organometalate, alkylene oxide and water are present and these methods, inter alia, are disclosed in copending U.S. Pat. No. 4,579,982, of J. R. Briggs and J. H. Robson, herein incorporated by reference.

Since the conventional hydrolysis reaction can occur, various procedures can be employed to enhance the yield of the monoalkylene glycol product. For instance, the alkylene oxide can be introduced into a liquid organometalate-containing phase. Also, large amounts of the organometalate may be provided per unit volume of reactor. Generally, the mole ratio of organometalate to alkylene oxide fed into the reactor is at least about 0.001:1, and is often at least about 0.01:1. In some instances it may be desired to provide the organometalate in an amount greater than that required on a stoichiometric basis for reaction with the alkylene oxide present in the reaction zone. Thus, the mole ratio of organometalate to alkylene oxide may be 5:1 or even 10:1 or greater. Because of the volume of reactor and amount of organometalate required, economics usually dictate that the mole ratio of organometalate to alkylene oxide will be within the range of about 0.01:1 to 2.0:1, say, about 0.05:1 to 1.5:1. With the greater amounts of organometalate chemical kinetics dictate that the relative portion of the alkylene glycol formed through formation of the vicinal dioxyalkylene organometalate is enhanced.

The ratio of water to alkylene oxide may also be relatively low in order to enhance the portion of the alkylene oxide that reacts with the organometalate; however, at too low ratios, the concentration of alkylene glycol may be sufficiently high that significant amounts of di- and polyglycols are formed. Hence, a balance exists for optimizing the amount of alkylene glycol formed from the vicinal dioxyalkylene organometalate and the existence of such alkylene glycol concentrations that undesirable amounts of di- and polyalkylene glycols are formed. However, in general, the ratio of water to alkylene oxide can be lower than that employed for conventional hydrolysis with achieving at least as great a selectivity to monoalkylene glycol. The ratio of water to alkylene oxide is often in the range of about 0.5:1 to 50:1, say, about 1:1 to 20:1, preferably about 3:1 to 10:1.

In the two-phase procedures the organometalate-containing phase or the aqueous phase may be the continuous phase. Preferably the discontinuous phase is highly dispersed and is in the form of small bubbles to enhance the interface areas between the phases. Accordingly, devices to enhance the dispersion may be employed such as agitators, spargers, and the like.

In a still further method, the reactions between the organometalate and alkylene oxide and the dioxyalkylene organometalate and water may be conducted in a homogeneous liquid phase. The organo-containing cation is selected so that the organometalate is preferentially soluble in an immiscible organic liquid such as dichloromethane, 1,1,2-trichloroethane, hexane, toluene, etc., but yet it is sufficiently soluble in water that selectivity-enhancing amounts of the organometalate can be provided in the reaction menstruum. The effluent from the reaction zone can then be contacted with an immiscible organic solvent to recover the organometalate by extraction. For example, tetra-n-butyl and tetra-n-hexyl ammonium metalate salts exhibit sufficient hygroscopicity that they can be dissolved in large amounts in a water and ethylene oxide-containing reaction medium, and they have sufficient organophilicity, e.g., in toluene, to be extracted using conventional extraction apparatus from the effluent from the reaction zone. Further details are provided in U.S. Pat. No. 4,571,440 of B. T. Keen, et al., herein incorporated by reference.

In yet a further method, the organometalate may be provided with a solid phase through association with electropositive complexing sites on a solid support such as described in U.S. patent application Ser. No. 594,368, filed Mar. 28, 1984.

When employing organometalates in a non-aqueous phase, e.g., when associated with a solvent, the addition of a small amount of a metalate anion-containing material, which may be a water soluble metalate, enhances the stability of the organometalate such as disclosed in U.S. Pat. No. 4,579,983, of B. T. Keen, herein incorporated by reference.

The pH of the reaction menstruum is frequently maintained relatively neutral, e.g., at a pH of between about 5 and 11, preferably about 6 to 10.5, and most often the pH is in the range of about 6 to 10. With some metalate anions, such as the vanadates and molybdates, the pH of the medium can be determinative of the species present. For example, in strong bases the orthovanadate may predominate, but at neutral conditions metavanadate will exist. In another example, more acidic media promote the formation of polynuclear molybdates which often have less, if any, activity towards forming vicinal dioxyalkylene organometalates.

The pH may be maintained within the desired range by the addition of acid or base, or the addition of buffers as is well known in the art; however, the presence and nature of salts should be considered since the cation may displace the organo-containing cation. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor. For example, the pH of the water component may be adjusted to the desired level prior to admixing with the alkylene oxide.

The maintenance of the pH within the desired ranges can also have a secondary effect of enhancing the stability of the organometalate.

The processes of this invention are carried out at temperatures sufficient to enable the reaction between the alkylene oxide and the organometalate. The temperature, however, should not be so great that the organo-containing cation and metalate anion are unduly adversely affected. Accordingly, the process is often carried out at a temperature between about 20° C. and about 220° C. or 250° C. Most often, the reaction is carried out at a temperature between about 50° C. and 200° C., say, about 80° C. to 180° C. The reaction between the vicinal dioxyalkylene organometalate and water is believed to proceed more rapidly even at low temperatures than the reaction between alkylene oxide and the organometalate to form the dioxyalkylene organometalate.

The processes may be conducted at subatmospheric, atmospheric or superatmospheric pressure. However, often pressures are employed which are sufficient to maintain the vicinal dioxyalkylene organometalate and the organometalate product in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The production of alkylene glycol according to this invention may be conducted in the presence of a gas, which is preferably inert. Gases which may be employed include air, carbon dioxide, nitrogen, argon and the like. Carbon dioxide is often present during the hydrolysis of alkylene oxide by the very nature of the process and the source of the alkylene oxide (especially by partial oxidation of ethylene). Frequently, it is desired to maintain the mole ratio of carbon dioxide to alkylene oxide less than 0.1:1, particularly less than 0.05:1, unless it is desired to affect the pH of the reaction menstruum. Carbon dioxide can be used in certain amounts to enhance the selectivity provided by vanadate anion such as disclosed in U.S. patent of B. T. Keen, herein incorporated by reference.

Generally, the reaction is conducted for a period of time sufficient to ensure that substantially all the alkylene oxide is reacted. The amount of time required to accomplish the substantially complete reaction is determined by the other conditions employed including temperature, amount of reactants present, and the like. The reaction may be carried out for very short periods of time; e.g., fractions of a second, and, if desired, may be carried out for periods of up to hours, e.g. about 0.01 second to 5 hours, preferably about 1 second to 30 minutes.

The alkylene glycol-containing product may contain organometalate. The organometalate can be extracted from the alkylene glycol-containing stream by contact with an immiscible liquid in which the organometalate is preferentially soluble. For further discussion see U.S. Pat. No. 4,571,440. Alternatively, the alkylene glycol-containing stream may be contacted with, for instance, an anion exchange resin such as a chloride-loaded DOWEX (TM) MSA-1 resin available from the Dow Chemical Company to recover the metalate anion. This resin can be separated and regenerated with the metalate anion being returned to the hydrolysis reaction zone. The alkylene glycol can be recovered and refined in a suitable manner. See for further discussion U.S. Pat. No. 4,560,813, of J. A. Collier, herein incorporated by reference. It is also possible to recover the organometalate material by distillation (e.g., evaporation or fractional distillation) from the alkylene glycols. When employing higher temperature separation processes, e.g., above about 100° or 120° C., the provision of small amounts of water enhances the stability of many metalate anions.

The alkylene glycol may be recovered from the reaction effluent in any convenient manner. Typically, the water is removed in a series of multiple-effect evaporators and the alkylene glycol is further refined by vacuum distillation.

The vicinal dioxyalkylene organometalates of this invention may also find application in reactions with alcohols, e.g., methanol, ethanol, and n-butanol, to form ethers. Reactions with carboxylic acids, amides and the like may also provide useful products.

The following examples are provided to assist in the understanding of the invention and are not in limitation thereof. All percentages and parts of solid are by weight and all percentages and parts of liquids and gases are by volume, unless otherwise indicated.

EXAMPLE 1

A 300 milliliter Parr reactor was charged with 5.73 grams of bis[bis(triphenylphosphine)iminium]tungstate and 40 milliliters of dichloromethane which had previously been dried with calcium hydride, distilled and subsequently dried over 4A molecular sieves. Ten milliliters of propylene oxide which had previously been dried over calcium hydride were also charged to the reactor. The reaction mixture was then heated to 140° C. for approximately three hours and cooled with cooling water to about 20° to 25° C. (ambient temperature). After cooling, the volatiles were removed under vacuum (approximately 1 to 2 millibars absolute) and a solid residue was provided. The solid residue was washed twice with 30 milliliters of diethyl ether and dried under vacuum. Approximately 5.8 grams of product, an adduct of propylene oxide and bis[bis(triphenylphosphine)iminium]tungstate were recovered. The product was subjected to proton nuclear magnetic resonance (nmr) spectroscopy to confirm the identity of the product using a Varian XL-100 nmr Spectrometer and dideuterated dichloromethane solvent with a probe temperature of about 25° to 30° C. (Unless otherwise stated, the nmr spectroscopy is proton nuclear magnetic spectroscopy as set forth above.)

EXAMPLE 2

A mixture of 5.0 grams of bis[bis(triphenylphosphine)iminium]molybdate and 20 milliliters of dichloromethane had been dried according to the procedure described in Example 1. This mixture was allowed to stand overnight in the presence of 4 A molecular sieves, and the mixture was decanted into a 300 milliliter Parr reactor. Approximately 4 milliliters of propylene oxide which had previously been dried over calcium hydride were charged to the reactor. The reaction mixture was refluxed for about 6 hours, cooled. The solvent was removed from the liquid by stripping under vacuum (approximately 1 to 2 millibars absolute). The solid residue, approximately 4.8 grams, was the adduct of propylene oxide and bis[bis(triphenylphosphine)iminium]molybdate. The product was subjected to nmr spectroscopy to confirm the identity of the product using a Perkin-Elmer R-20B nmr Spectrometer.

EXAMPLE 3

To 5.08 grams of bis[bis(triphenylphosphine)iminium]molybdate and 45 milliliters of dichloromethane (dried by distillation from calcium hydride) was added 4 A molecular sieves. This liquid mixture was decanted into a 300 milliliter Parr reactor, and the molecular sieves were washed with 25 milliliters of dried dichloromethane which was then added to the reactor. Approximately 5 milliliters of styrene oxide which had been dried over powdered calcium hydride were then charged to the reactor. The mixture was heated to about 100° C. for about 3 hours, then cooled to about 20° to 25° C. using cooling water. The cooled mixture was stripped of volatiles using a vacuum (about 1 to 2 millibars absolute). The residue was washed three times with 30 milliliters of diethyl ether, then recrystallized from a mixture of 20 milliliters of dichloromethane and 40 milliliters of diethyl ether. The product, the styrene oxide adduct of bis[bis(triphenylphosphine)iminium]molybdate, was analyzed by nmr spectroscopy using the equipment described in Example 1 to confirm its identity.

EXAMPLE 4

A 300 milliliter Parr reactor was charged with 5.08 grams of bis[bis(triphenylphosphine)iminium]tungstate, 66 milliliters of dichloromethane (dried) and 10.26 grams of styrene oxide. The mixture was heated to 140° C. for slightly over 3 hours and then cooled to about 20° to 25° C. with cooling water. The volatiles were stripped from the mixture under vacuum (about 1 to 2 millibars absolute). The residue was washed four times with 20 milliliters of diethyl ether, dried and then washed and dried under vacuum (about 1 to 2 millibars absolute). The product, the styrene oxide adduct of bis[bis(triphenylphosphine)iminium]tungstate, was analyzed by nmr spectroscopy using the equipment described in Example 1 to confirm its identity.

EXAMPLE 5A

To a 300 milliliter Parr reactor having a polyethylene tetrafluoride liner was added 4.70 grams of bis[bis(triphenylphosphine)iminium]tungstate and 45 milliliters of dried dichloromethane. The mixture was cooled to about 15° C. and 12.57 grams of ethylene oxide at a temperature of about −78° C. were added. The reaction mixture was heated to about 100° C. for about 3.5 hours and the pressure during the reaction increased to about 100 pounds per square inch gauge. The reactor was then cooled to 17° C., and the solvent was stripped under vacuum (1-2 millibars absolute). The residue was a viscous oil with an entrained precipitate containing the ethylene oxide adduct of bis[bis(triphenylphosphine)iminium]tungstate.

EXAMPLE 5B

A solution of 5.01 grams of bis[bis(triphenylphosphine)iminium]tungstate in about 25 milliliters of dichloromethane (dried) was prepared in a glass flask containing 4 A molecular sieves. This solution was allowed to stand over a weekend and then decanted into a 300 milliliter Parr reactor. The molecular sieves were washed twice with 10 milliliters of dichloromethane (dried) and the dichloromethane used in the washing was charged to the reactor.

A solution of ethylene oxide in dichloroethane was prepared in a glass flask by bubbling ethylene oxide through the solvent, and the concentration of the ethylene oxide was determined by gas chromatography. Approximately 41 milliliters of the solution containing 0.49 grams of ethylene oxide were charged to the reactor.

The reaction mixture was stirred and heated to 140° C. for three hours and then cooled. The volatiles were stripped from the mixture under vacuum (about 1 to 2 millibars absolute). About 5.48 grams of a solid residue were recovered and washed three times with 30 milliliters of diethyl ether. The washed solids were dried under vacuum (about 1 to 2 millibars absolute). The product was analyzed by infrared and nmr spectroscopy.

EXAMPLE 6

A 100 milliliter glass flask equipped with a condenser was purged with argon and charged with 5.0 milliliters of dichloromethane (dried) and about 1.06 gram of bis[bis(triphenylphosphine)iminium]molybdate. The mixture was cooled to about 10° C. and about 6.21 grams of ethylene oxide were poured into the flask. The mixture was refluxed (about 35° C.) for about 6 hours using a dry ice/acetone condenser. The condenser was connected to a drying tube containing 4 A molecular sieves. The solvent and excess ethylene oxide were stripped from the reaction mixture at the end of the six-hour period using a vacuum (about 1 to 2 millibars absolute). The produce, the ethylene oxide adduct of bis[bis(triphenylphosphine)iminium]molybdate, was analyzed by nmr spectroscopy using the equipment described in Example 1 to confirm its identity.

The techniques described in Examples 1 to 6 are useful in preparing other alkylene oxide adducts of organometalates. Table I provides examples of the preparation of other vicinal dioxyalkylene organometalates. The alkylene oxide is provided in a stoichiometric excess unless otherwise indicated.

TABLE I

| Example | Organometalate | Alkylene Oxide | Solvent |
| --- | --- | --- | --- |
| 7 | bis[(tetra-n-propyl)ammonium] molybdate | ethylene oxide | dichloromethane |
| 8 | bis[bis(triphenylphosphine)iminium] tungstate | ethylene oxide (1 mole per mole of tungstate) | toluene |
| 9 | bis[bis(triphenylphosphine)iminium] molybdate | cyclohexane oxide | dichloromethane |
| 10 | bis[(tetra-n-hexyl)phosphonium] molybdate | ethylene oxide | dichloromethane |
| 11 | bis[(tri-n-hexyl)ammonium] molybdate | ethylene oxide | toluene |
| 12 | bis[(triethyl)sulfonium] tungstate | ethylene oxide | toluene |
| 13 | bis[(tetra-n-hexyl)arsonium] molybdate | ethylene oxide | toluene |
| 14 | (tetra-n-hexyl)ammonium vanadate | ethylene oxide | diethyl ether |

TABLE I-continued

| Example | Organometalate | Alkylene Oxide | Solvent |
|---|---|---|---|
| 15 | bis[(triphenylphosphine)iminium] vanadate | ethylene oxide | toluene |

The vicinal dioxyalkylene organometalates can also be prepared from compounds of the formula:

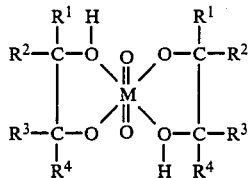

by reaction with a base of the formula $R^5R^6R^7X$. The examples in Table II provide vicinal dioxyalkylene organometalates.

TABLE II

| Example | M | $R^1$ | $R^2$ | $R^3$ | $R^4$ | X | $R^5$ | $R^6$ | $R^7$ | Solvent |
|---|---|---|---|---|---|---|---|---|---|---|
| 16 | Mo | H | H | H | $CH_3$ | N | $CH_3$ | $CH_3$ | $CH_3$ | benzene |
| 17 | W | H | H | H | H | N | $C_2H_5$ | $C_2H_5$ | $C_2H_5$ | dichloromethane |

The preparation of many of the vicinal dioxyalkylene organometalates of this invention involves the use of an organometalate starting material. The following examples demonstrate the preparation of various organometalates useful for preparing vicinal dioxyalkylene organometalates.

EXAMPLE 18

Into a glass flask was charged a mixture of 30 grams of bis(triphenylphosphine)iminium chloride in 600 milliliters of distilled water having a temperature of about 55° C. A previously prepared solution of 6.32 grams of sodium molybdate dihydrate in 100 millliliters of distilled water having a temperature of about 55° C. was added to the flask and the reaction medium was stirred for about 75 minutes while maintaining the temperature at about 55° C. The reaction medium was allowed to cool to about 42° C. A white precipitate existed. The precipitate was filtered, washed three times with water (50° C.), dried in air, and then dried under vacuum (about 1 to 2 millibars absolute) over phosphorous pentoxide. The product was recovered in a yield of 74 percent (23.91 grams) and had a melting point of 165°–170° C. The product was identified by infrared spectrographic analysis to be bis[bis(triphenylphosphine)iminium]molybdate.

EXAMPLE 19

Approximately 2.35 grams of bis(triphenylphosphine)iminium chloride were dissolved in 45 milliliters of distilled water at a temperature of about 55° C. in a glass flask. To this solution was added a previously prepared solution of 0.67 grams of sodium tungstate dihydrate dissolved in 5 milliliters of water at about 50° C. contained in a glass flask. The flask that contained the sodium tungstate was rinsed with 5 milliliters of distilled water, and the wash water was added to the reaction mixture. The reaction mixture was stirred for 90 minutes while maintaining the temperature at about 55° C. After cooling the reaction mixture to about 45° C., the precipitate formed in the reaction medium was removed by filtration. The filtrate was washed three times with distilled water at about 40° C., dried in air and then dried under vacuum (about 1 to 2 millibars absolute) over phosphorous pentoxide. The product was recovered in a yield of about 56% (1.50 gram). The product was determined by infrared spectrographic analysis to be bis[bis(triphenylphosphine)iminium]tungstate.

EXAMPLE 20

A solution of about 5.0 grams of sodium molybdate dihydrate and 20 milliliters of water was prepared in a glass flask. A solution of about 7.0 grams of silver nitrate in 20 milliliters of water was separately prepared in another glass flask and then added to the sodium molybdate-containing solution. A white precipitate immediately appeared. The reaction mixture was stirred for five minutes, and the precipitate was then recovered by filtration. The recovered precipitate was washed with water, then with acetone and finally with diethyl ether. The washed solid was dried in air by suction. The solid (about 7.7 grams) which is silver molybdate, was added to the flask containing a previously prepared solution of about 18 grams of tetra-n-hexylammonium iodide in 75 milliliters of dichloromethane and 5 milliliters of distilled water. The reaction mixture was stirred for about 95 minutes while covered with a paper bag to reduce exposure to light. The insoluble material was filtered and washed several times with dichloromethane. The solvent was removed by stripping under vacuum (about 1 to 2 millibars absolute). The product, bis(tetra-n-hexylammonium)molybdate was identified by infrared spectrographic analysis and was recovered in a yield of 76% (14.0 grams).

EXAMPLE 21

In one glass flask 4.0 grams of silver nitrate were dissolved in 25 milliliters of water, and in another flask, 3.9 grams of sodium tungstate dihydrate were dissolved in 25 milliliters of water. The solutions were combined and stirred for about five minutes. The precipitate was recovered by filtration and washed three times with about 30 milliliters of water, three times with about 30 milliliters of acetone and three times with diethyl ether to recover about 5.4 grams of silver tungstate.

In a further glass flask about 9.37 grams of tetra-n-heptylammonium chloride were dissolved in 125 milliliters of dichloromethane and about 5.37 grams of the silver tungstate were added with 8 milliliters of water. The reaction mixture was stirred for about 6.5 hours while being covered with a paper bag to reduce exposure to light. The silver chloride contained in the reaction medium was removed by filtration using Hi-Flo ™ filter aid cake on a frit. The frit was washed with dichloromethane and added to the remaining liquid. The remaining liquid is stripped under vacuum (about 1 to 2 millibars absolute) to yield about 9.3 grams of product, bis[(tetra-n-heptyl)ammonium]tungstate. The identity of the product was confirmed by infrared spectrographic analysis.

EXAMPLE 22

Into a glass flask was added 5.0 grams of bis(triphenylphosphine)iminium chloride and 109 milliliters of water. The mixture was stirred and heated to 60° C. and the pH was adjusted to 10 with an aqueous solution containing 15 percent sodium hydroxide.

A sodium vanadate solution was separately prepared in another glass flask by mixing about 1.06 grams of sodium metavanadate with 44 milliliters of water and heating the mixture to about 60° C. The pH was adjusted to 10 with the sodium hydroxide solution. The solutions were reheated to 60° C. and the vanadate solution was added to the bis(triphenylphosphine)iminium solution and the mixture was stirred for about 40 minutes while maintaining a temperature of about 60° C. The reaction mixture was cooled in a water bath to about 42° C. while continuing the stirring for about 48 minutes. The insoluble material was isolated by filtration and then washed twice with distilled water at a temperature of about 42° C. It was dried in air by suction and then in a desiccator over phosphorous pentoxide. The product, bis(triphenylphosphine)iminium vanadate, was obtained in the amount of 4.5 grams.

EXAMPLE 23

In a glass flask about 5.11 grams of silver nitrate were dissolved in about 20 milliliters of distilled water. In another glass flask, about 3.64 grams of sodium molybdate were dissolved in about 20 milliliters of distilled water, and the silver nitrate solution was poured into it. The mixture was stirred for about 5 minutes and then filtered at about 10° C. using a 15 milliliter Buchner funnel with frit. The retentate was washed three times with 10 milliliters of distilled water, three times with 10 milliliters of acetone and three times with 10 milliliters of diethyl ether. After sucking dry, the filter cake weighed about 5.64 grams.

A solution of about 15.0 grams of (tetra-n-octadecyl)ammonium bromide and 62.5 milliliters of dichloromethane was prepared in a glass flask by heating. Then, while stirring at 30° C., the previously prepared filter cake was introduced into the solution. After six hours, the solution was heated to reflux (at ambient pressure). The solution was filtered, and the filtrate was stripped of volatiles under vacuum (about 1 to 2 millibars absolute). About 15.01 grams of bis(tetra-n-octadecylammonium)molybdate were recovered and its identity was confirmed by infrared spectrographic analysis.

EXAMPLE 24

Into a glass flask containing at about 50° C. a previously prepared solution of about 1 gram of silver nitrate in 3 milliliters of distilled water was added a solution of about 0.72 grams of sodium metavanadate in 30 milliliters of distilled water which was at a temperature of about 60° C. The admixture was stirred for about 10 minutes while the temperature remained at about 50° C. to 60° C. An orange-yellow precipitate formed and was recovered by filtration. The solid was washed three times with distilled water, three times with acetone and three times with diethyl ether then dried in air under suction.

In another glass flask, a solution of 2.55 grams of tetra-n-hexylammonium iodide in 30 milliliters of dichloromethane was prepared. About 3 milliliters of water were added and then, while stirring at ambient temperature, the previously prepared silver vanadate was added. The stirring continued for about 1.5 hours while under a paper bag to reduce the exposure to light. The precipitate changed color from an orange-yellow appearance to pale yellow during the course of the process. The precipitate was recovered by filtration and washed thoroughly with dichloromethane using Hi-Flo TM filter aid and the wash liquid was added to the filtrate. The filtrate was then stripped under vacuum (about 1 to 2 millibars absolute). The identity of the product, (tetra-n-hexyl)ammonium vanadate, was confirmed by infrared spectrographic analysis.

EXAMPLE 25

In a glass flask, a previously prepared solution of about 1.2 grams of tetra-n-propylammonium iodide in 25 milliliters of water was added to 1.2 grams of silver molybdate while stirring at ambient temperature (i.e., about 20° C. to 25° C.). After about 15 minutes, the insoluble material was removed by filtration. The remaining, colorless solution was stripped of volatiles at a temperature not exceeding 30° C. under vacuum (about 1 to 2 millibars absolute). The recovered liquid was washed with diethyl ether, dried under vacuum (about 1 to 2 millibars absolute) at 50° C., and cooled to $-78°$ C. to crystallize the product. The product remained crystalline when warmed to room temperature. The product, bis(tetra-n-propylammonium)molybdate, was obtained in the amount of about 0.96 grams and, because of its hygroscopic nature, was maintained in a desiccator. The identity of the product was confirmed by infrared spectrographic analysis.

The vicinal dioxyalkylene organometalates of the invention are particularly useful for generating monoalkylene glycols when contacted with water. The vicinal dioxyalkylene organometalates are typically those which can be prepared from an organometalate and alkylene oxide. The following examples illustrate the preparation of alkylene glycols from alkylene oxides, water and organometalates. The enhanced selectivity to monoalkylene glycols is believed to evidence the formation of the vincinal dioxyalkylene organometalate from the organometalate and alkylene oxide and its subsequent reaction with water to produce alkylene glycol. Had the adduct of the invention not been formed, greater amounts of dialkylene glycol resulting from the reaction of alkylene oxide with alkylene glycol would have been observed.

Unless otherwise stated, all the examples were conducted using a 300 milliliter Parr reactor at a hydrolysis ratio (weight of water to weight of alkylene oxide) of 1.0.

The analysis of the reaction product was conducted by temperature programmed gas chromatography using 10 ft $\times \frac{1}{8}$" stainless steel column packed with Chromosorb 101 (60/80 mesh). Sample injections (2-3 microliters) were made from a sample of 1.5 to 2.0 grams of hydrolysis product to which had been added 0.12 to 0.15 gram of 2-ethyl-1,3-hexanediol as internal standard. Alternatively, the analysis was conducted by preparing the samples by adding about 2 weight percent 1,3-butanediol as an internal standard. Approximately 50 microliters of this admixture are added to 1.0 milliliter of Regisil TM (BSTFA) (N,N-bis trimethylsilyl trifluoroacetamide), available from the Regis Chemical Company, Morton Grove, Ill., in a serum vial and mixed for at least about 12 hours. The weight percent monoethylene glycol, diethylene glycol and triethylene glycol are determined by standard vapor phase chromatography using a Hewlett Packard 5880 ™ gas chromatograph equipped with a four meter by ⅛ inch (0.32 centimeters) (outside diameter) stainless steel column packed with 20 percent OV-101 methylsilicone stationary liquid phase supported on 80/100 mesh Chromosorb W HP ™ both available from Supelco, Inc., Bellefonte, Pa.

Selectivities are defined as [G/(M+D+T)] times 100% where G is the weight of the glycol in question, M is the weight of monoalkylene glycol, D is the weight of dialkylene glycol and T is the weight of trialkylene glycol.

EXAMPLE 26

The reactor was charged with 16.43 grams of ethylene oxide, 16.59 grams of distilled water, 0.82 grams of bis[(tetra-n-hexyl)ammonium]molybdate and 26.17 grams of toluene. A two-phase reaction medium resulted, and the mixture was continuously stirred to maintain a dispersion of the phases. The reaction mixture was heated to 170° C. and the pressure rose to about 220 psig and then fell to a steady pressure of 120 psig within about 13 minutes. After about 50 minutes, the heating was ceased and the reactor was cooled with ice water. In about 10 minutes, the stirring was ceased and the reactor was opened to reveal two separated layers. The aqueous layer was analyzed to contain monoethylene glycol (79% selectivity), diethylene glycol (19% selectivity) and triethylene glycol (2% selectivity).

EXAMPLE 27

The reactor was charged with 16.04 grams of ethylene oxide, 16.19 grams of distilled water, 2.92 grams of bis[(tetra-n-hexyl)ammonium]molybdate and 26.24 grams of toluene. A two-phase reaction medium resulted and the mixture was continuously stirred to maintain a dispersion of the phases. The reaction medium was heated to about 140° C. for slightly over one hour. During the reaction, the pressure increased to about 160 psig and then fell to about 40 psig. The reactor was cooled with cooling water and then ice water to about 5° C. and opened. The aqueous layer was recovered and analyzed to contain monoethylene glycol (89% selectivity), diethylene glycol (11% selectivity), and triethylene glycol (less than 1% selectivity).

EXAMPLE 28

The reactor was charged with 15.4 grams of ethylene oxide, 15.4 grams of distilled water, 0.775 grams of bis[(tetra-n-heptyl)ammonium]tungstate and 27.67 grams of toluene. A two-phase reaction medium resulted and the mixture was continuously stirred to maintain a dispersion of the phases. The reaction mixure was heated to about 140° C. for about 3 hours. During the reaction the pressure increased to about 155 psig and dropped to about 50 psig. The reactor was then cooled with cooling water and then ice water to about 2° C. The aqueous layer was recovered and analyzed to contain monoethylene glycol (68% selectivity), diethylene glycol (26% selectivity) and triethylene glycol (6% selectivity).

EXAMPLE 29

The reactor was charged with 14.8 grams of ethylene oxide, 15.4 grams of water, 0.95 grams of bis[(tetra-n-hexyl)ammonium]molybdate and 30.75 grams of dimethyl sulfoxide. A single liquid phase reaction mixture resulted. The reaction mixture was heated to about 140° C. with stirring and maintained at that temperature for about 47 minutes during which time the pressure rose to about 130 pisg and fell to about 20 psig. The reaction mixture was cooled with ice water and analyzed to contain monoethylene glycol (95% selectivity) and diethylene glycol (5% selectivity). No triethylene glycol was detected.

EXAMPLE 30

A 50 milliliter, round bottom, glass flask was charged with 10.0 grams of bis(triphenyl phosphine)iminium vanadate and 10 milliliters of dichloromethane. The solution was cooled to below 10° C., and 6.91 grams of ethylene oxide (about 0° C.) were then added. After weighing the flask, 6.91 grams of distilled water (about 0° C.) were added to form a two-phase reaction mixture. The mixture was stirred rapidly and refluxed (about 35° C.) under a dry ice/acetone condenser for about 7 hours. The mixture was then allowed to stand at ambient temperature overnight. The aqueous layer was removed from the organic layer and analyzed to contain monoethylene glycol. No diethylene glycol or triethylene glycol was detected.

EXAMPLE 31

A 100 milliliter, round bottom, glass flask was charged with about 3.01 grams of bis[bis(triphenylphosphine)iminium]molybdate and about 14.35 grams of ethylene oxide were condensed into the flask. Thereafter, 10 milliliters of dichloromethane (0° C.) were added. The mixture was allowed to stand for about three hours. The solvent and ethylene oxide were then stripped under vacuum (about 1 to 2 millibars absolute). Approximately 10 milliliters of 1,1,2-trichloroethane and 0.18 grams of distilled water were added to the residue and refluxed at ambient pressure for about 2 hours and 20 minutes under a dry ice/acetone condenser. The condenser was washed with 1,1,2-trichloroethane and then water. The aqueous layer was separated and was analyzed to contain monoethylene glycol. No diethylene glycol or triethylene glycol was detected.

EXAMPLE 32

The reactor was charged with 15.75 grams of ethylene oxide, 15.46 grams of distilled water, 29.94 grams of dimethyl sulfoxide and 1.54 grams of bis(tetraoctadecyl)ammonium molybdate. The reaction mixture was heated to 140° C. for about 80 minutes while stirring. The reaction mixture was then cooled with cooling water and ice water and analyzed to contain monoethylene glycol (92.5% selectivity) and diethylene glycol (7.5% selectivity).

EXAMPLE 33

The reactor was charged with 20.0 grams of propylene oxide, 20.3 grams of distilled water, 26.7 grams of dichloromethane and 2.01 grams of bis[bis(triphenylphosphine)iminium]molybdate. The reaction mixture was continuously stirred and heated to 140° C. for nearly 4 hours. During this time the pressure increased to about 190 psig and then fell to about 160 psig. The reaction mixture was then cooled with cooling water and ice water. The organic and aqueous layers were separated. The organic layer was washed with distilled water and this wash water was combined with the separated aqueous phase. The combined aqueous phases were found to contain about 20.7 grams of monopropylene glycol.

EXAMPLE 34

The reactor was charged with 2.01 grams of bis[bis(-triphenylphosphine)iminium]molybdate, 20.0 grams of tiles were distilled from the flask, recovering ethylene glycol at a bottom temperature of about 95° C. to 98° C. under a pressure of about 0.5 millibar absolute.

Table III, which follows, provides a further expansion of the principles illustrated in the preceding examples.

TABLE III

| Example No. | Organo-Metalate | Alkylene Oxide | Mole Ratio/ Metalate:Oxide | Solvent | Water Addition | Predominant Product |
|---|---|---|---|---|---|---|
| 37 | tetra-n-hexylammonium vanadate (pH 10) | ethylene oxide | 1:5 | dichloromethane | initial | monoethylene glycol |
| 38 | bis[bis(triphenyl-phosphine)iminium]-tungstate | ethylene oxide | 1:1 | toluene | after reaction to form adduct | monoethylene glycol |
| 39 | bis(tetra-n-propyl-ammonium) molybdate | ethylene oxide | 1:2 | water | initial | monoethylene glycol |
| 40 | bis[bis(triphenyl-phosphine)iminium]-molybdate | 1,2-epoxy butane | 0.006:1 | dichloromethane | initial | 1,2-dihydroxybutane |
| 41* | tetra-n-hexylammonium rhenate | ethylene oxide | 1:1 | toluene | after reaction to form adduct | monoethylene glycol |
| 42 | tetra-n-hexylammonium molybdate | propylene oxide | 1:1 | dichloromethane | after reaction to form adduct | monopropylene glycol |

*When conducted as a single step reaction, no enhancement in monoethylene glycol selectivity was observed.

distilled water, 20.15 grams of styrene oxide and 26.79 grams of dichloromethane. The reaction mixture was continuously stirred and heated to about 140° C. for about 2 hours and 50 minutes. During this time the pressure rose to about 165 psig. Thereafter, the reaction mixture was cooled by cooling water and ice water, and the aqueous phase separated. The aqueous phase was analyzed to contain styrene glycol.

EXAMPLE 35

A stirred, 50 milliliter, round bottom, glass flask, equipped with a condenser was charged with 1.0 grams of bis[bis(triphenylphosphine)-iminium]molybdate, 5 milliliters of cyclohexene oxide, 1.0 milliliter of distilled water and 5.0 milliliters of 1,1,2-trichloroethane. The mixture was heated to reflux (at ambient pressure) while cooling the condenser with dry ice/acetone for three hours. The heating and stirring was stopped and reinitiated about 15 to 16 hours later and continued for about 7.5 hours. A brown-colored solution was produced. Water and cyclohexene oxide were removed from the mixture under vacuum (about 1 to 2 millibars absolute) at about 35° C. to 40° C. A white solid precipitated on the side of the flask. The solid had a melting point of about 100.5° C. to 101.5° C. Analysis by infrared spectroscopy indicated that the product was exclusively 1,2-trans-dihydroxy-cyclohexane.

EXAMPLE 36

To a stirred, 50 milliliter, round bottom glass flask equipped with a condenser were charged 4.9 grams of bis(tetra-n-hexylammonium)molybdate and 20 milliliters of toluene (distilled from calcium hydride). The resulting mixture was chilled to about 0.5° C. in ice water and about 9.52 grams of ethylene oxide (about 0° C.) were added. The mixture was refluxed at ambient pressure for about 5 hours. The volatiles were stripped under vacuum (about 1 to 2 millibars absolute) and a viscous green mass of material was obtained. To this material was added 20 milliliters of toluene and about 0.107 milliliters of water and the mixture was heated to reflux for two hours at ambient pressure. The initial green color of the solution changed to a light brown. The condenser was washed with about 2 milliliters of water and then with 5 milliliters of toluene. The vola- The following example is provided for comparison purposes.

EXAMPLE 43

The reactor was charged with 15.19 grams of distilled water, 30 milliliters of toluene and (after cooling to about 0°–5° C.) 14.97 grams of ethylene oxide. The mixture was stirred and heated to about 140° C. for about 3.5 hours, cooled to about 2° C. in ice water. The aqueous layer was recovered and analyzed to contain monoethylene glycol (56% selectivity), diethylene glycol (33% selectivity) and triethylene glycol (11% selectivity).

EXAMPLES 44 TO 47

The following stock solutions were prepared:

Solution A: 2.0 grams BTHAM* and 5.0 grams dichloromethane

Solution B: 2.0 grams BTHAM and 5.0 grams tetrahydrofuran

Solution C: 2.0 grams BTHAM and 5.0 grams tetrahydrofuran

Solution D: 0.4 grams BTHAM and 4.0 grams tetrahydrofuran

Solution E:** 4.4 grams ethylene oxide and 46 milliliters dichloromethane

Solution F:** 4.4 grams ethylene oxide and 46 milliliters tetrahydrofuran

*BTHAM is (bis(tetrahexyl)ammonium) molybdate
**chilled (about 0°–5° C.)

The processes were conducted using stainless steel microreactors having a length of about 9 centimeters and an outside diameter of about 1.3 centimeters. Aliquots of one of the stock solutions A to D and one of the stock solutions E and F were introduced using suitably sized syringes into a microreactor (both pre-dried), the microreactor sealed and introduced into a constant temperature bath at 60° C. for two hours under a reciprocating motion. The microreactors were then withdrawn, cooled to about room temperature over night, opened, water charged, resealed and again heated in the bath at 60° C. for one hour. Thereafter, the microreactors were cooled and the contents analyzed. The details are provided in Table IV.

TABLE IV

| Example | Stock Solution Identity | Stock Solution Amount (ml) | Stock Solution Identity | Stock Solution Amount (ml) | Water ml | MEG Selectivity % |
|---|---|---|---|---|---|---|
| 44 | A | 5.0 | E | 1.0 | 0.072 | 98.3% |
| 45 | B | 5.0 | F | 0.66 | 0.036 | 100% |
| 46 | C | 5.0 | F | 0.66 | 0.14 | 100% |
| 47 | D | 4.0 | F | 1.6 | 0.15 | * |

*incomplete conversion of ethylene oxide

EXAMPLES 48 TO 52

In these examples, the following general procedure was used. Into the reactor was introduced a previously prepared solution of the organometalate in solvent using vacuum to assist in the transfer. The water was then charged and the autoclave purged with nitrogen and vented. Cooled ethylene oxide (liquid) was injected into the autoclave under nitrogen pressure. The reaction menstruum was stirred at a stirrer rotation rate of about 800 rpm. The autoclave was pressurized to about 3.5 atmospheres absolute, heated and then maintained at substantially a constant temperature for about one hour. The pressure was allowed to rise. After cooling, a portion of the aqueous phase was withdrawn for analysis. The details of the examples are provided in Table V.

TABLE V

| Example | Metalate Anion-Containing Material Identity | Amount, g | Water, g | CH$_2$Cl$_2$, g | Ethylene Oxide, g | Temp. °C. | Selectivity to MEG, % |
|---|---|---|---|---|---|---|---|
| 48 | (PPN) VO$_3$* | 8.3 | 33.0 | 33.0 | 33.0 | 140° C. | 73.7% |
| 49 | (PPN)$_2$ MoO$_4$** | 8.3 | 33.0 | 33.0 | 34.0 | 140° C. | 86.7% |
| 50 (control) | — | — | 33.0 | 33.0 | 33.0 | 140° C. | 58.7% |
| 51 (control) | Na$_2$MoO$_4$*** | 1.38 | 33.0 | 33.0 | 34.0 | 140° C. | 87.4% |
| 52 | (PPN)$_2$MoO$_4$ | 7.9 | 33.0 | 33.0 | 33.0 | 100° C.**** | 83.4% |

*bis(triphenylphosphine)iminium metavanadate
**bis[bis(triphenylphosphine)iminium]molybdate
***preferentially soluble in water
****reactor temperature maintained for about two hours

EXAMPLES 53 TO 56

In these examples the following general procedure was used. A stock solution of ethylene oxide (33 grams) and water (71 grams) was prepared in a serum bottle and maintained at about 2° C. A separate stock solution of toluene (10 grams) and bis(tetrahexylammonium)-molybdate (BTHAM) (4.5 grams) was prepared in 120 cubic centimeter serum bottles at room temperature (about 22° C.). Aliquots of each stock solution were introduced into chilled (about 2° C.) stainless steel tubular microreactors (exterior dimensions of about 9.6 millimeters by 76 millimeters) that are capable of being immersed in a constant temperature bath. The microreactors were purged with nitrogen prior to the introduction of the materials. After introducing the materials, the reactors were sealed and immersed in the bath while under a reciprocating motion to promote agitation. After about one hour, the microreactors were withdrawn from the bath and cooled to about 0° C. in an ice bath. Samples of the aqueous phase were withdrawn and analyzed. The details of the examples are provided in Table VI.

TABLE VI

| Example | Water, g | Toluene, g | Ethylene Oxide, g | BTHAM, g | Temp., °C. | Selectivity to MEG, % |
|---|---|---|---|---|---|---|
| 53 | 0.38 | 1.42 | 0.17 | 0.64 | 110° C. | 97.3 |
| 54 | 1.47 | 0.36 | 0.69 | 0.16 | 110° C. | 91.5 |
| 55 | 0.38 | 1.42 | 0.17 | 0.64 | 140° C. | 98.5 |
| 56 | 1.47 | 0.36 | 0.69 | 0.16 | 140° C. | 91.2 |

EXAMPLE 57

Into an evacuated (about 10 millibar absolute) glass vessel at room temperature, containing one gram of bis(triphenylphosphine)-iminium metavanadate, was introduced a mixture of 50 weight percent ethylene oxide and 50 weight percent argon until the pressure in the vessel had increased by about 500 to 550 millibars. Then a mixture of 10 milliliters of water and 50 milliliters of 1,1,2-trichloroethane was syringed into the reactor. The reactor was heated to reflux while stirring magnetically. After about one hour a circulating pump was turned on. The system was shut down after about 3 hours and allowed to sit overnight. Then an additional 4 milliliters of ethylene oxide were added and the system restarted. After about 2 hours, the solvent layer was distilled under vacuum and heat with several washings of 1,1,2-trichloroethane (72.3 grams of solvent layer recovered). An aqueous layer of 41.4 grams was obtained and a sample was analyzed to contain monoethylene glycol.

EXAMPLE 58

Under an argon atmosphere 5.28 grams of tetrahexylammonium molybdate were added to a 100 milliliter glass flask. The flask was then cooled to about 10° C. and 9.66 grams of ethylene oxide were poured into the flask and then about 9.61 grams of distilled water (about 0° C.) were added. The flask was purged with argon and then refluxed using dry ice in an acetone cooled condenser for 5 hours then the condenser was allowed to warm to room temperature. The apparatus was allowed to stand overnight. About 9 milliliters of water were added with shaking and then about 30 milliliters of toluene were added and three distinct phases formed.

The aqueous layer was found to contain monoethylene glycol.

EXAMPLES 57 TO 70

Substantially the same procedure described in Examples 53 to 56 was employed in these examples. The details are provided in Table VII. In all Examples except 61 and 62, the stirring was at about 420 rpm. In Example 61, the stirrer rate was about 840 rpm and in Example 62, 300 rpm. In all but Example 63, the maximum temperature of the reaction menstruum was about 140° C. In Example 63, it was about 170° C.

TABLE VII

| Example | Ethylene Oxide, g | Water g | Metalate-Anion Containing Material Identity | Metalate-Anion Containing Material Amount, g | Solvent Identity | Solvent Amount | Selectivity to MEG, % |
| --- | --- | --- | --- | --- | --- | --- | --- |
| 59 | 16.0 | 16.2 | A | 0.81 | T | 30 ml | 76.2% |
| 60* | 16.0 | 16.1 | A | 0.80 | T | 30 ml | 79.4% |
| 61 | 16.3 | 16.2 | A | 0.81 | T | 30 ml | 74.6% |
| 62 | 16.3 | 16.4 | A | 0.81 | T | 30 ml | 75.7% |
| 63 | 16.4 | 16.6 | A | 0.82 | T | 30 ml | 78.9% |
| 64 | 16.0 | 15.5 | A | 4.90 | T | 30 ml | 93.7% |
| 65 | 15.5 | 15.5 | B | 1.5 | A | 30 g | 91.6% |
| 66 | 15.7 | 15.5 | B | 1.5 | D | 30 g | 92.5% |
| 67** | 16.2 | 16.3 | C | 1.0 | H | 30 g | 61.8% |
| 68 | 15.6 | 15.5 | B | 1.5 | H | 30 g | 64.8% |
| 69 | 15.8 | 15.2 | B | 1.5 | E | 30 g | 64.2% |
| 70 | 14.9 | 15.1 | A | 1.5 | M | 45 g | 87.5% |

*Heating for ½ hour, insufficient time for complete reaction of ethylene oxide.
**Organic phase contains catalyst layer
Metalate Anion-Containing Materials
A Bis(tetra-n-hexylammonium)molybdate
B Bis(tetra-n-octadecylammonium)molybdate
C Bis(tetra-n-dodecylammonium)molybdate
Solvent
H Hexane
E Dibutyl ether
M 20 g toluene and 25 g triphenylphosphine oxide
T Toluene
A Acetone
D Dimethylsulfoxide

EXAMPLE 71

Substantially the same procedure described in Example 5 was employed except that the toluene-containing layer was recovered from a reaction medium and was used in a subsequent reaction medium. The aqueous layer from the reaction yielding the toluene was extracted twice with about 10 milliliters of toluene and a portion of the rinse toluene was also used in the subsequent reaction.

The first run employed about 1.5 grams of bis(tetra-n-hexylammonium)molybdate. The details are provided in Table VIII.

The low selectivities in runs 2 to 5 are believed to be due to difficulty in obtaining a good and rapid phase separation. A more preferable solvent would be, e.g., dichloromethane.

TABLE VIII

| Run | Ethylene Oxide, g | Water, g | Recycle Toluene, g | Rinse Toluene, g | Selectivity to MEG, % |
| --- | --- | --- | --- | --- | --- |
| 1 | 16.0 | 15.4 | (Fresh Toluene, 30 g) | | 82.3% |
| 2 | 15.8 | 15.5 | 27.8 | 3.6 | 43.2% |
| 3 | 15.6 | 15.3 | 28.6 | 2.9 | 32.2% |
| 4 | 15.8 | 15.4 | 26.4 | 5.1 | 44.2% |
| 5 | 15.5 | 15.5 | 30.0 | 1.8 | 47.0% |

EXAMPLES 72 TO 76

These experiments were carried out in a U-shaped ⅜" (0.95 cm) (outside diameter) stainless steel reactor. Generally, the reactor was charged from both ends with the desired volume of resin as a slurry in water. The volume of wet resin charged to the reactor as well as the reactor length are as listed in Table IX. The resin was held in place by stainless steel frits placed at each end of the bed. Chilled (5° C.) water, ethylene oxide and alkali metalate (when employed) were charged into a feed tank (internal volume 900 cc) and kept pressurized at 25 pounds per inch gauge pressure with nitrogen. Stainless steel tubing (1/16") (0.16 cm) carried the reactants from the feed tank to the reactor and the products from the reactor to the product receiver. A back pressure regulator was used to keep the system pressure at 200 pounds per inch gauge pressure (nitrogen). The flow of reactants to the reactor was controlled by a dual piston high pressure liquid chromatography pump. The reaction products were cooled to ambient temperature by immersing a coiled section of a reactor exit line in a water bath. The U-shaped reactor was immersed (typically only to the level of the resin in the reactor) in a stirred constant temperature oil bath.

Conversion of the alkylene oxide was 100 percent except where noted and monoalkylene glycol selectivities are as shown in Table IX. The anion exchange resin catalysts were prepared using aqueous solutions of the sodium or potassium metalate. In all instances, the chloride concentration of the wash effluent after the exchange with the metalate anion was less then about 5 ppm as determined by ion chromatography. The general preparation procedure was to suspend the resin in an aqueous solution of the metalate (e.g. about 5 wt. percent) at room temperature with stirring for about one-half hour, wash, and repeat contact with the metalate by eluting an aqueous solution of the metalate through a glass column packed with the resin until the chloride was completely exchanged. The resin was then thoroughly washed with water.

TABLE IX

| Ex. | REACTANT SOLUTION | | | Resin Type/ Metalate Loaded | Volume Wet Resin in Reactor (cc) | Approximate Reactor Length (cm.) | Flow Rate ml/min. | Reaction Temp. °C. | Monoalkylene Glycol Selectivity % |
|---|---|---|---|---|---|---|---|---|---|
| | Alkylene Oxide/Wt. % | Water (Wt. %) | Alkali Metalate/ppm wt. | | | | | | |
| 72 | EO/9.2 | 90.8 | Na$_2$MoO$_4$/6 | DOWEX MSA-1/MoO$_4^{-2}$ | 15 | 33 | 1.0 | 146 | 98.4 |
| 73 | EO/10.1 | 89.9 | Na$_2$MoO$_4$/140 | DOWEX MSA-1/MoO$_4^{-2}$ | 15 | 33 | .72 | 152 | 96.7 |
| 74 | EO/7.7 | 92.3 | Na$_2$WO$_4$/102 | DOWEX MSA-1/WO$_4^{-2}$ | 19.5 | 43 | 1.0 | 131 | 98.2 |
| 75 | EO/20.0 | 80.0 | Na$_2$WO$_4$/170 | DOWEX MSA-1/WO$_4^{-2}$ | 19.5 | 43 | .80 | 135 | 94.1 |
| 76 (comparative) | EO/12.5 | 87.5 | None | DOWEX MSA-1/V$_2$O$_7^{-4}$ | 14.5 | 33 | 1.00 | 121 | 97.9 |

EO = Ethylene oxide

EXAMPLE 77

Into a glass vessel was charged 400 grams of an aqueous solution (about 15 wt. %) of Cat-Floc T-1 TM polymer available from Calgon, Inc., having an average molecular weight of about 300,000 and heterocylic nitrogen which is a quaternary ammonium group in association with chloride anion. About 1600 milliliters of water were added to the solution followed by about 80 milliliters of wet DOWEX TM MSC-1 cationic exchange resin having sulfonic functionality available from The Dow Chemical Company. The mixture was stirred at a temperature of about 50° C. overnight. The liquid was decanted and 1200 milliliters of water and 400 grams of the aqueous solution containing Cat-Floc T-1 TM polymer were added. The mixture was stirred while heating at about 70° to 80° C. for approximately five hours. The liquid was decanted and another mixture was formed with 1200 milliliters of water and heated to about 70° to 80° C. for five hours with stirring. The liquid was decanted and the solid resin was washed twice with 500 milliliters of water.

The metalate was incorporated into the resin by slurrying it in about one liter of an aqueous solution containing about five weight percent of sodium molybdate. This slurry was heated to about 50° C. for 3 hours while stirring. The liquid was decanted and this slurrying process was conducted two more times. After decanting the liquid, the resin was loaded into a glass column (about 2.5 centimeters in diameter) and about 1.5 liters of an aqueous solution containing three weight percent sodium molybdate was pumped through the column at a relatively low rate (in the neighborhood of 5 milliliters per minute).

The resin was employed for the hydrolysis of ethylene oxide using an apparatus such as described in respect to Examples 72 to 76. The reactor length was about 33 centimeters with the resin loosely packed therein. Glass wool was placed between the resin bed and each of the frits to prevent plugging the frits. The solution for feeding to the reactor contained about 1800 grams of water, 180 grams of ethylene oxide and about 0.6 grams of sodium molybdate. The rate of feed was varied from about 0.2 to 1.0 milliliter per minute. The reactor was maintained at about 125° C., and pressure of about 14 atmospheres gauge. At a feed rate of about 0.2 milliliters per minute, the conversion of ethylene oxide was substantially complete, and the product was analyzed for selectivity to monoethylene glycol which was about 93 percent.

EXAMPLE 78

About 50 grams of Davison 59 TM silica gel available from Davison Chemical Division of W. R. Grace Co. (about 8 to 20 mesh U.S. Sieve Series), were changed to a 500 milliliter glas erlenmeyer flask and 253 grams of a solution of 2 parts by weight of concentrated hydrochloric acid to one part by weight of water were added. A condenser (water-cooled) was placed on the flask. The solution was refluxed for three hours and the liquid decanted. The solids were washed three times with water and placed in a glass column having a diameter of about 2.5 centimeters and length of about 70 centimeters. Water was then pumped through the silica gel bed until the pH was in the range of about 6 to 7 (approximately 4 liters of water). About 500 milliliters of methanol were provided to the column to dehydrate the silica gel, and the solids were recovered but maintained covered with methanol.

The acid activated silica gel was separated from the methanol by decanting, and it was placed with 300 milliliters of toluene into a previously dried, 500 milliliter round bottom flask. The flask was purged with nitrogen, equipped with a condenser and then heated to reflux. About 35 milliliters of overhead (as a liquid) were recovered. The mixture was cooled to about 60° C. and 8.6 grams of (N,N-dimethyl-3-amino)propyl trimethoxysilane were added dropwise to the solution. The solution was then refluxed overnight and about 10 milliliters of overhead material were collected. After cooling to about 60° C., another 8 grams of the silane were added dropwise and the solution was refluxed for four hours and cooled to about 60° C. About one milliliter of water was added and the solution was again refluxed overnight. After cooling to about 60° C., about 5 grams of the siloxane were added and the solution was refluxed for about four hours. After cooling to about 60° C., one milliliter of water was added and the solution was refluxed overnight. The solution was then cooled and filtered to recover the solids which were then dried for about one hour at 150° C. Analysis indicated that the silica gel had about 1.21 meq/g of amine sites.

Approximately 30 grams of the silica gel having the amine sites were changed with about 100 milliliters of 1,2-dimethoxyethane into a stirred, round bottom flask. To this mixture was added 15 milliliters of a previously prepared solution containing 10 milliliters of iodomethane and 5 milliliters of 1,2-dimethoxyethane. The mixture was allowed to stand overnight and then, with stirring, another 5 milliliters of iodomethane were added, and the mixture was heated to about 60° C. It was then cooled and the solids recovered by filtration and washed with water. The washed solids were placed in a glass column having a diameter of about 2.5 centimeters and a length of about 45 centimeters.

About two liters of an aqueous solution containing about 60 grams of sodium molybdate were slowly pumped (about 3 to 5 milliliters per minute) through the column at a temperature of about 80° C. The solids were again washed and then vacuum dried. Elemental analysis revealed that the solids contained about 1.46 percent molybdenum.

This material was used for the hydrolysis of ethylene oxide using an apparatus such as described in respect to Examples 72 to 76. The reactor length was about 33 centimeters with the resin loosely packed therein. Glass wool was placed between the bed and the frits. The solution used for the hydrolysis contained about 1800 milliliters of water, about 180 milliliters of ethylene oxide and about 0.25 grams of sodium molybdate. The rate of feed was varied between about 1.0 and 0.5 milliliters per minute. The reactor was maintained at about 125° C. under a pressure of about 14 atmospheres gauge. At a feed rate of about 0.5 milliliters per minute, the conversion of ethylene oxide was substantially complete and the selectivity to monoethylene glycol was about 95 percent. After about one and one-half days the pressure increased and the reactor was shut down. The solids bed had compressed and fines were observed.

EXAMPLE 79

Into an Erlenmeyer flask were added about 76 grams of 20 weight percent aqueous solution of Cat-Floc T-1 ™ polymer and about 100 grams of Ludox HS-40 ™ colloidal silica available from E. I. duPont de Nemours & Co., Inc. A precipitate immediately formed. The slurry was heated at about 70° to 80° C. for two hours while stirring. The liquid was then decanted, water added to form anothe slurry, and the slurry heated at about 70° to 80°. This procedure was repeated several times. Then the solids were again slurried in water and the pH adjusted to about 7 with molybdic acid. The solution was again heated to about 60° to 80° C. for thirty hours.

The solid was recovered by filtration and placed in a glass column (about 2.5 centimeters diameter) and a dilute aqueous solution of sodium molybdate was passed through the column until virtually no chloride was detected in the eluant.

The solids were then recovered and employed for the hydrolysis of ethylene oxide using an apparatus such as described in respect to Examples 72 to 76. About 6.6 grams of the solids (dry) were loosely packed in a reactor about 25 centimeters in length. Water was pumped through the reactor to expel air and glass wool placed between the solids and frits. The feed mixture to be used contained about 1800 milliliters of water, about 180 milliliters of ethylene oxide and about 0.25 grams of sodium molybdate. The rate of feed was varied from about 0.3 to 1.0 milliliters per minute. The temperature of the reactor was maintained at about 125° C. with a pressure of about 14 atmospheres gauge. At a feed rate of about 0.33 milliliters per minute, the conversion of ethylene oxide was substantially complete and the selectivity to monoethylene glycol was about 95 to 96 percent. When the temperature was increased to about 140° C. with a feed rate of about 0.5 milliliters per minute, the conversion remained substantially complete but the pressure increased and the selectivity was about 94 percent. The reactor was shut down and, upon inspection, the frit on the outlet side of the reactor was plugged.

It is claimed:

1. A process for making alkylene glycols of the formula

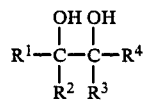

comprising contacting a vicinal dioxyalkylene organometalate compound of the formula:

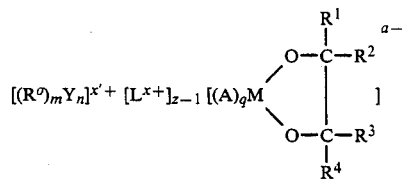

wherein $x'$ is the integer 1; $[(R^o)_m Y_n]^{x'+}$ comprises a cation having a positive change of $x'$ selected from the group consisting of ammonium or phosphonium cations of the formulae:

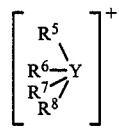

wherein Y is nitrogen or phosphorus, sulfonium cations of the formula:

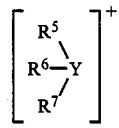

wherein Y is sulfur, and bis(hydrocarbyl-phosphine)imminiums of the formula:

$$[(R_3^9 P)_2 N]^+$$

wherein $R^5$ to $R^9$ are the same or different and comprise hydrogen or hydrocarbyl substituents selected from the group consisting of aliphatic or aromatic substituents having from 1 to 20 carbon atoms with the proviso that at least one of $R^5$ to $R^9$ is a hydrocarbyl substituent and that at least one of $R^5$ to $R^9$ contains sufficient carbon atoms that said vicinal dioxyalkylene organometalate is soluble in an organic solvent; L is a cation which has a positive charge of X wherein X is 1, which is selected from the group consisting of:

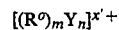

as defined above, alkaline metal, quaternary ammonium and quaternary phosphonium cations; z is 1 to 4; a is from 1 to 4; and

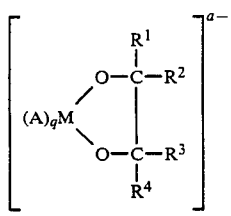

is an anion having a negative charge of a selected from the group consisting of anions of the formula $[VO_4C_2H_4]^{-1}$, $[V_2O_8C_2H_4]^{-4}$, $[C_2H_4O_2WO_3]^{-2}$, $[(C_2H_4O_2)_2WO_2]^{-2}$, $[V_2O_8C_2H_5]^{-3}$,

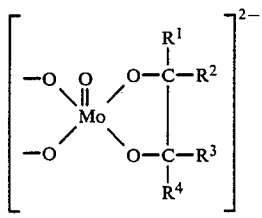

and

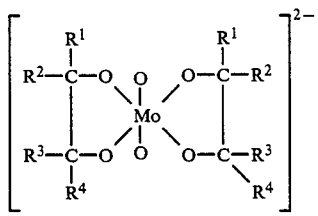

wherein $R^1$ to $R^4$ are the same or different and are hydrogen, alkyl of between 1 and about 10 carbons, monocyclic or bicyclic aryl having up to about 12 carbons, alkyl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms, with liquid water or water vapor at a temperature and pressure sufficient to provide the alkylene glycol wherein $R^1$, $R^2$, $R^3$ and $R^4$ correspond to $R^1$, $R^2$, $R^3$ and $R^4$ of said vicinal dioxyalkylene organometalate compound.

2. The process of claim 1 wherein an organometalate of the formula:

$[(R)_mY_n]^{x'+}[L^{x+}]_{z-1}[(A)_qM(O)]^{a-}$ wherein $[(R)_mY_n]$ and $[L^{x+}]_{z-1}$ are cations as defined in claim 1, and $[(A)_qM(O)]^{a-}$ is an anion of negative charge a— wherein a— is from −1 to −4, M is a polyvalent metal selected from the group consisting of molybdenum, vanadium and tungsten, and A represents one or more substituents to fill the remaining valencies (q) of M and is the same or different and is selected from the group consisting of double bonded oxygen and —O—, is coproduced with the alkylene glycol.

3. The process of claim 1 wherein the metal as in the metalate has a nucleophilicity with respect to ethylene oxide greater than that exhibited by rhenium as in rhenate anion under the same conditions.

4. The process of claim 3 wherein the metal as in the metalate has an electrophilicity with respect to ethylene oxide greater than that exhibited by vanadium as in orthovanadate under the same conditions.

5. A process for making a vicinal dioxyalkylene organometalate compound of the formula:

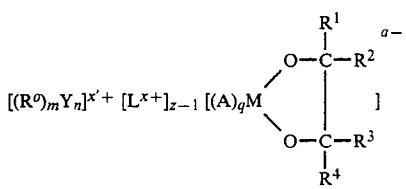

wherein x' is the integer 1; $[(R^o)_mY_n]^{x'+}$ comprises a cation having a positive charge of x' selected from the group consisting of ammonium or phosphonium cations of the formulae:

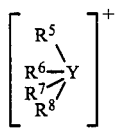

wherein Y is nitrogen or phosphorus, sulfonium cations of the formula:

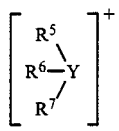

wherein Y is sulfur, and bis(hydrocarbyl-phosphine) iminiums of the formula:

$[(R_3^9P)_2N]^+$ wherein $R^5$ to $R^9$ are the same or different and comprise hydrogen or hydrocarbyl substituents selected from the group consisting of aliphatic or aromatic substituents having from 1 to 20 carbon atoms with the proviso that at least one of $R^5$ to $R^9$ is a hydrocarbyl substituent and that at least one of $R^5$ to $R^9$ contains sufficient carbon atoms that said vicinal dioxyalkylene organometalate is soluble in an organic solvent; L is a cation which has a positive charge of X wherein X is 1, which is selected from the group consisting of:

$[(R^o)_mY_n]^{x'+}$ as defined above, alkaline metal, quaternary ammonium and quaternary phosphonium cations; z is 1 to 4; a is 1 to 4; and

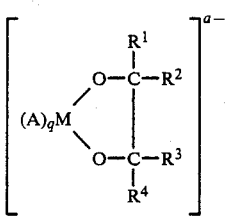

is an anion having a negative charge of a selected from the group consisting of anions of the formula

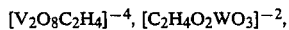

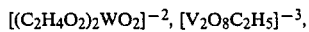

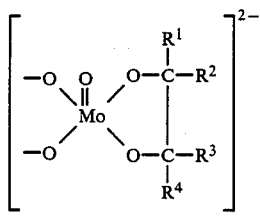

and

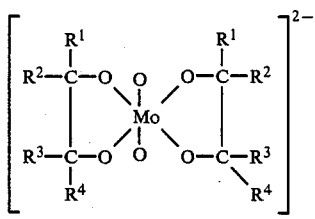

wherein $R^1$ to $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms, by contacting alkylene oxide of the formula:

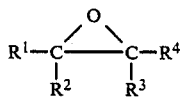

wherein $R^1$ to $R^4$ are as defined above with an organometalate of the formula:

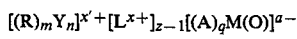

wherein $[(R)_mY_n]$ and $[L^{x+}]_{z-1}$ represent cations as defined above, and $[(A)_qM(O)]^{a-}$ is an anion having a negative charge of a— wherein a— is from −1 to −4, M is a polyvalent metal selected from the group consisting of molybdenum, vanadium and tungsten, and A represents one or more substituents to fill the remaining valencies (q) of M is the same or different and is selected from the group consisting of double bonded oxygen and —O—, at a temperature and pressure sufficient to form said vicinal dioxyalkylene organometalate compound.

6. The process of claim 5 which is conducted in the substantial absence of water.

7. The process of claim 6 wherein the metal as in the metalate has a nucleophilicity with respect to ethylene oxide greater than that exhibited by rhenium as in rhenate anion under the same conditions.

8. The process of claim 7 wherein the metal as in the metalate has an electrophilicity with respect to ethylene oxide greater than that exhibited by vanadium as in orthovanadate under the same conditions.

9. The process of claim 4 in which the organometalate is subsequently contacted with alkylene oxide of the formula:

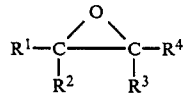

wherein $R^1$ to $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms, at a temperature and pressure sufficient to form the vicinal dioxyalkylene organometalate compound.

10. The process of claim 4 which is conducted in the presence of alkylene oxide of the formula:

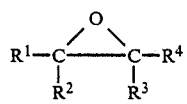

wherein $R^1$ to $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms, at a temperature and pressure sufficient to react the alkylene oxide with the organometalate.

* * * * *

UNITED STATES PATENT AND TRADEMARK OFFICE
CERTIFICATE OF CORRECTION

PATENT NO. : 4,822,925
DATED : April 18, 1989
INVENTOR(S) : John R. Briggs, John H. Robson It is certified that error appears in the above-identified patent and that said Letters Patent is hereby corrected as shown below:

Column 1, line 32, "183" should read --1983--.

Column 4, line 51, "oxides or tungsten" should read --oxides of tungsten--.

Column 5, line 33, "sould" should read --should--.

Column 8, line 37, "iin" should read --in--.

Column 8, line 40, "a" should read --as--.

Column 12, line 60, "$[(R^9_3P)_2N]30$" should read --$[(R^9_3P)_2N]^+$--.

Column 16, line 34, "reation" should read --reaction--.

Claim 1, line 8 (Column 38, line 28, "change" should read --charge--.

UNITED STATES PATENT AND TRADEMARK OFFICE
CERTIFICATE OF CORRECTION

PATENT NO. : 4,822,925
DATED : April 18, 1989
INVENTOR(S) : John R. Briggs, John H. Robson It is certified that error appears in the above-identified patent and that said Letters Patent is hereby corrected as shown below:

Claim 1, line 16 (Column 38, line 49), "miniums" should read --iniums--.

Signed and Sealed this

Twenty-eighth Day of January, 1992

Attest:

HARRY F. MANBECK, JR.

Attesting Officer

Commissioner of Patents and Trademarks